United States Patent
Liska et al.

(10) Patent No.: US 10,253,045 B2
(45) Date of Patent: Apr. 9, 2019

(54) CRYSTALLINE FORMS OF A THERAPEUTIC COMPOUND AND USES THEREOF

(71) Applicant: Kala Pharmaceuticals, Inc., Waltham, MA (US)

(72) Inventors: Tadeas Liska, Auburndale, MA (US); Elizabeth Enlow, Waltham, MA (US); Jinsoo Kim, Brighton, MA (US); Winston Ong, Stoneham, MA (US)

(73) Assignee: Kala Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 15/529,969

(22) PCT Filed: Nov. 24, 2015

(86) PCT No.: PCT/US2015/062491
§ 371 (c)(1),
(2) Date: May 25, 2017

(87) PCT Pub. No.: WO2016/086026
PCT Pub. Date: Jun. 2, 2016

(65) Prior Publication Data
US 2017/0313724 A1 Nov. 2, 2017

Related U.S. Application Data

(60) Provisional application No. 62/084,682, filed on Nov. 26, 2014.

(51) Int. Cl.
*C07D 519/00* (2006.01)
*A61K 31/5025* (2006.01)
*A61P 27/02* (2006.01)

(52) U.S. Cl.
CPC ........ *C07D 519/00* (2013.01); *C07B 2200/13* (2013.01)

(58) Field of Classification Search
CPC .................................................. C07D 519/00
See application file for complete search history.

(56) References Cited

U.S. PATENT DOCUMENTS

| | | | |
|---|---|---|---|
| 8,273,741 | B2 | 9/2012 | Sakai et al. |
| 9,056,057 | B2 | 6/2015 | Popov et al. |
| 9,988,386 | B2 * | 6/2018 | Ong ..................... C07D 487/04 |
| 2010/0029619 | A1 | 2/2010 | Uchikawa et al. |
| 2010/0249119 | A1 | 9/2010 | Masaaki et al. |
| 2010/0311729 | A1 | 12/2010 | Capraro et al. |
| 2013/0316001 | A1 | 11/2013 | Popov et al. |
| 2013/0316006 | A1 | 11/2013 | Popov et al. |
| 2016/0137646 | A1 | 5/2016 | Ong et al. |

FOREIGN PATENT DOCUMENTS

| | | |
|---|---|---|
| WO | 2008/016131 | 2/2008 |
| WO | 2008/016192 | 2/2008 |
| WO | 2010/032880 A2 | 3/2010 |
| WO | 2014/197313 A2 * | 12/2014 |

OTHER PUBLICATIONS

Osaadon et al. Eye (2014) 28, 510-520.*
Chang et al. Surv Ophthalmol. Sep. 2012 ; 57(5): 415-429. (Year: 2012).*
Triantafylla et al. Clinical Ophthalmology 2014:8 1187-1198. (Year: 2014).*
Miyamoto N et al. "Discovery of N-[5-({2-[(cyclopropylcarbonyl)amino]imidazol[1,2-b]pyridinazin-6-yl}oxy)-2-methylphenyl]-1,3-dimethyl-1H-pyrazole-5-carboxamide (TAK-593), a highly potent VEGFR2 kinase inhibitor", Bioorgan Med Chem 21:2333-2345, 2013.
Okaniwa M et al. "Design and synthesis of novel DFG-out RAF/vascular endothelial growth factor receptor 2 (VEGFR2) inhibitors. 1. Exploration of [5,6]-fused bicyclic scaffolds." J Med Chem 55:3452-3478, 2012.
CAS Registry No. 1005840-87-8 STN entry date Feb. 29, 2008; N-[6-[3-[[(1,3-dimethyl-1H-pyrazol-5-yl)carbonyl]amino]-4-fluorophenoxy]imidazo[1,2-b]pyridazin-2-yl]-4-methyl-1-piperazineacetamide.
CAS Registry No. 1005779-08-7, STN Entry Date: Feb. 29, 2008; N-[6-[3-(acetylamino)phenoxy]imidazo(1,2-b]pyridazin-2-yl-4-(1,1-dimethylethyl)-benzamide.
Fan et al., "Controlling the vasculature: angiogenesis, anti-angiogenesis and vascular targeting of gene therapy." Trends Pharmacol. Sci. 16:57-66, 1995.
Folkman, "Angiogenesis in cancer, vascular, rheumatoid and other disease." Nature Medicine 1:27-31, 1995.
Roskoski R, "Vascular endothelial growth factor (VEGF) signaling in tumor progression." Crit. Rev. Oncol./Hematol. 62:179-213, 2007.
Bryn et al. "Pharmaceutical Solids: A strategic approach to regulatory considerations," Pharma. Res. 12:945-954, 1995.
Bernstein "Convention for naming polymorphs" In Polymorphism in molecular crystal [IUCR monographs on crystallography], 2002, p. 8.

(Continued)

*Primary Examiner* — Emily A Bernhardt
(74) *Attorney, Agent, or Firm* — K&L Gates LLP; Louis C. Cullman; Michelle Glasky Bergman

(57) ABSTRACT

Disclosed herein are certain crystalline forms of Compound 5, N-(5-((2-(4-(2-oxa-7-azaspiro[3.5]nonan-7-yl)butanamido)imidazo[1,2-0]pyridazin-6-yl)oxy)-2-methylphenyl)-1,3-dimethyl-1/-/-pyrazole-5-carboxamide, as well as pharmaceutical compositions comprising the crystalline forms. The present disclosure further relates to methods for treating or preventing diseases or disorders using the crystalline forms or pharmaceutical compositions thereof in a subject in need thereof, including diseases or disorders associated with abnormal or pathological angiogenesis and/or aberrant signaling of a growth factor signaling pathway (e.g., vascular endothelial growth factor (VEGF)), such as proliferative diseases and ocular diseases.

8 Claims, 10 Drawing Sheets

(56) References Cited

OTHER PUBLICATIONS

Brittain "X-ray diffraction III: pharmaceutical applications" Spectroscopy 16:14-18, 2001.
Ivanisevic et al. "Uses of X-Ray Powder Diffraction in the Pharmaceutical Industry" Pharmaceutical Sciences Encyclopedia: Drug Discovery Development, and Manufacturing. Jun. 25, 2010, pp. 1-42.
Fabian MA et al. "A small molecule-kinase interaction map for clinical kinase inhibitors," Nature Biotechnology 23:329-336, 2005.

* cited by examiner

CRYSTALLINE FORMS OF A THERAPEUTIC COMPOUND AND USES THEREOF

BACKGROUND

Growth factors play an important role in angiogenesis, lymphangiogenesis, and vasculogenesis, and they regulate angiogenesis in a variety of processes. Undesirable or pathological angiogenesis is associated with numerous diseases including diabetic retinopathy, psoriasis, cancer, rheumatoid arthritis, atheroma, Kaposi's sarcoma, and hemangioma. Angiogenic ocular conditions represent the leading cause of irreversible vision loss in developed countries. In the United States, for example, retinopathy of prematurity, diabetic retinopathy, and age-related macular degeneration are the principal causes of blindness in infants, working age adults, and the elderly, respectively.

Therefore, there is a need for new therapeutic compounds for the treatment of diseases associated with the aberrant signaling of growth factors and diseases associated with angiogenesis, such as cancer, macular degeneration, and diabetic retinopathy.

SUMMARY

Described herein is a crystalline compound N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, referred to herein as Compound 5 and shown in the formula below.

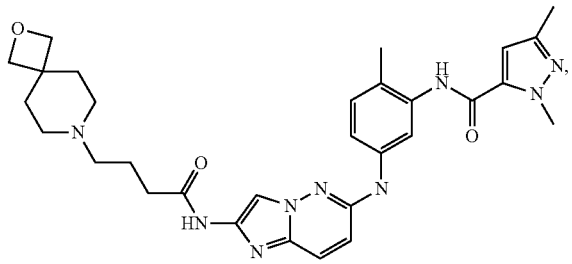 [SMILES: Cc1cc(C(=O)Nc2cc(Nc3ccc4nc(NC(=O)CCCN5CCC6(CC5)COC6)cn4n3)ccc2C)n(C)n1]

and pharmaceutical compositions thereof, and methods useful in treating and/or preventing diseases associated with abnormal angiogenesis and/or aberrant signaling of a growth factor (e.g., vascular endothelial growth factor (VEGF)). The diseases that may be treated and/or prevented by the inventive compounds, pharmaceutical compositions, kits, uses, and methods include proliferative diseases (e.g., cancers, benign neoplasms, inflammatory diseases, autoimmune diseases) and ocular diseases (e.g., macular degeneration, glaucoma, diabetic retinopathy, retinoblastoma, edema, uveitis, dry eye, blepharitis, and post-surgical inflammation).

Some embodiments include a crystalline form of Compound 5, wherein the crystalline form comprises crystalline Form I.

Some embodiments include a crystalline form of Compound 5, such as crystalline Form I, having an X-ray powder diffraction (XRPD) pattern with a largest peak in a range of about 4-4.6 2θ, and a second largest peak in a range of about 6-6.6 2θ.

Some embodiments include a crystalline form of Compound 5, wherein the crystalline form comprises crystalline Form II.

Some embodiments include a crystalline form of Compound 5, such as crystalline form II, having an X-ray powder diffraction (XRPD) pattern with a largest peak in a range of about 4.3-4.9 2θ, and a second largest peak in a range of about 3.1-3.7 2θ.

Some embodiments include a compound having the formula

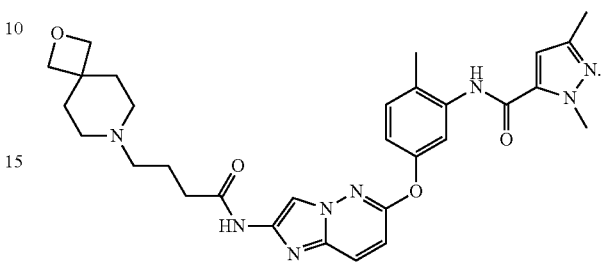

in crystalline Form II. In certain embodiments, the crystalline form may be crystalline Form II having an X-ray powder diffraction (XRPD) pattern with peaks at about 3.42, 4.59, and 13.71±0.2 degrees two-theta, or 25.78, 19.23, and 6.46±0.2 Å in d-spacing. In further embodiments, crystalline Form II further has XRPD peaks at about 17.13 and 17.82±0.2 degrees two-theta, or 5.17 and 4.97±0.2 Å in d-spacing. In further embodiments, crystalline Form II further has XRPD peaks at about 5.08, 7.36, 7.94, 10.20, 12.91, 14.72, and 25.64±0.2 degrees two-theta, or 17.40, 12.01, 11.12, 8.67, 6.85, 6.01, and 3.47±0.2 Å in d-spacing.

Some embodiments include a compound having the formula

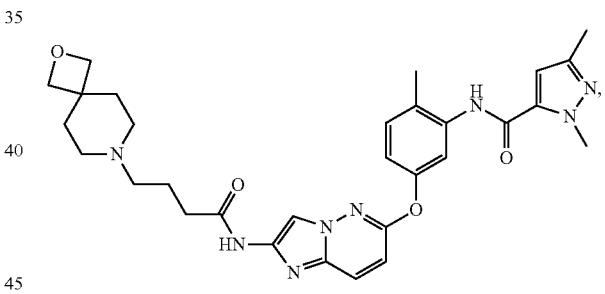

in crystalline Form II having an X-ray powder diffraction (XRPD) pattern with peaks at about 3.42, 4.59, 5.08, 7.36, 7.94, 10.20, 12.91, 13.71, 14.72, 17.13, 17.82, and 25.64±0.2 degrees two-theta, or 25.78, 19.23, 17.40, 12.01, 11.12, 8.67, 6.85, 6.46, 6.01, 5.17, 4.97, and 3.47±0.2 Å in d-spacing.

Some embodiments include N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide in crystalline Form II. In certain embodiments, the crystalline form is crystalline Form II having an X-ray powder diffraction (XRPD) pattern with peaks at about 3.42, 4.59, and 13.71±0.2 degrees two-theta, or 25.78, 19.23, and 6.46±0.2 Å in d-spacing. In further embodiments, crystalline Form II further has XRPD peaks at about 17.13 and 17.82±0.2 degrees two-theta, or 5.17 and 4.97±0.2 Å in d-spacing. In further embodiments, crystalline Form II further has XRPD peaks at about 5.08, 7.36, 7.94, 10.20, 12.91, 14.72, and 25.64±0.2 degrees two-theta, or 17.40, 12.01, 11.12, 8.67, 6.85, 6.01, and 3.47±0.2 Å in d-spacing.

Some embodiments include Crystalline Form II of a compound having the formula

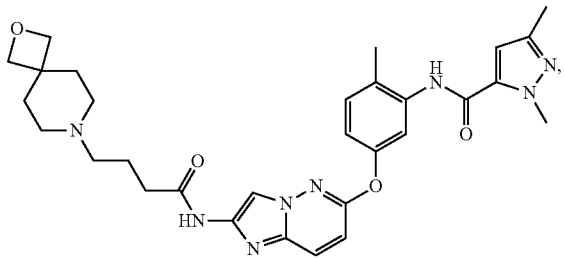

having the X-ray powder diffraction pattern as shown in FIG. 4.

Some embodiments include a compound having the formula

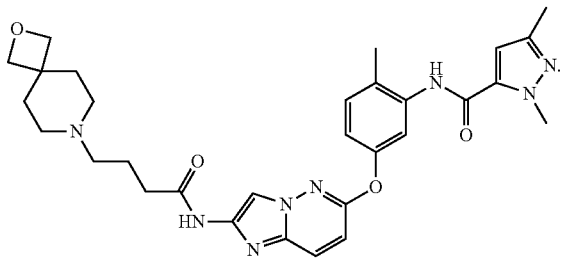

in crystalline Form I. In certain embodiments, the crystalline form is crystalline Form I having an X-ray powder diffraction (XRPD) pattern with peaks at about 4.31, 6.30, 13.90, 18.06, and 19.40±0.2 degrees two-theta, or 20.49, 14.02, 6.37, 4.91, and 4.57±0.2 Å in d-spacing. In further embodiments, crystalline Form I further has XRPD peaks at about 5.90, 16.01, and 16.25±0.2 degrees two-theta, or 14.96, 5.53, and 5.45±0.2 Å in d-spacing. In further embodiments, crystalline Form I further has XRPD peaks at about 9.37, 9.89, 11.80, 12.91, 14.84, 20.79, and 24.58±0.2 degrees two-theta, or 9.44, 8.94, 7.50, 6.85, 5.97, 4.27, and 3.62±0.2 Å in d-spacing.

Some embodiments include a compound having the formula

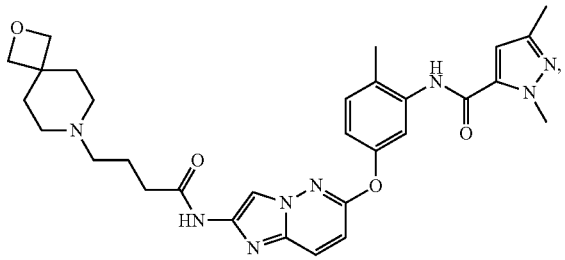

in crystalline Form I having an X-ray powder diffraction (XRPD) pattern with peaks at about 4.31, 5.90, 6.30, 9.37, 9.89, 11.80, 12.91, 13.90, 14.84, 16.01, 16.25, 18.06, 19.40, 20.79, and 24.58±0.2 degrees two-theta, or 20.49, 14.96, 14.02, 9.44, 8.94, 7.50, 6.85, 6.37, 5.97, 5.53, 5.45, 4.91, 4.57, 4.27, and 3.62±0.2 Å in d-spacing.

Some embodiments include N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide in crystalline Form I. In certain embodiments, the crystalline form is crystalline Form I having an X-ray powder diffraction (XRPD) pattern with peaks at about 4.31, 6.30, 13.90, 18.06, and 19.40±0.2 degrees two-theta, or 20.49, 14.02, 6.37, 4.91, and 4.57±0.2 Å in d-spacing. In further embodiments, crystalline Form I further has XRPD peaks at about 5.90, 16.01, and 16.25±0.2 degrees two-theta, or 14.96, 5.53, and 5.45±0.2 Å in d-spacing. In further embodiments, crystalline Form I further has XRPD peaks at about 9.37, 9.89, 11.80, 12.91, 14.84, 20.79, and 24.58±0.2 degrees two-theta, or 9.44, 8.94, 7.50, 6.85, 5.97, 4.27, and 3.62±0.2 Å in d-spacing.

Some embodiments include Crystalline Form I of a compound having the formula

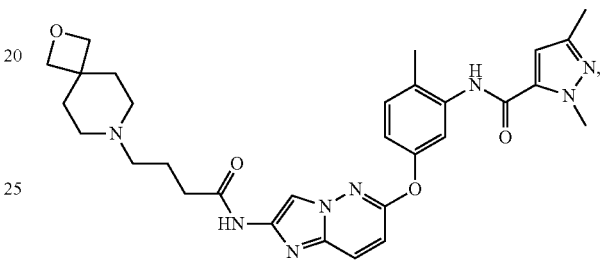

having the X-ray powder diffraction pattern as shown in FIG. 1.

Some embodiments include pharmaceutical compositions comprising crystalline Form I or crystalline Form II of N-(5-((2-(4-(2-oxa-7-azaspiro[3.5]nonan-7-yl)butanamido) imidazo[1,2-b]pyridazin-6-yl)oxy)-2-methylphenyl)-1,3-dimethyl-1H-pyrazole-5-carboxamide and optionally a pharmaceutically acceptable excipient. In certain embodiments, the pharmaceutical compositions described herein include an effective amount of crystalline Form I or crystalline Form II of N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide. The pharmaceutical composition may be useful for treating proliferative diseases (e.g., cancers, benign neoplasms, inflammatory diseases, autoimmune diseases) and/or ocular diseases (e.g., macular degeneration, glaucoma, diabetic retinopathy, retinoblastoma, edema, uveitis, dry eye, blepharitis, and post-surgical inflammation) in a subject in need thereof. The pharmaceutical composition may also be useful for inhibiting abnormal angiogenesis and/or aberrant signaling of a growth factor in a subject or cell.

In certain embodiments, disclosed herein are pharmaceutical compositions of crystalline Form I or crystalline Form II of Compound 5 that are suitable for topical administration. In other embodiments, the pharmaceutical compositions are suitable for injection. In another embodiment, the pharmaceutical compositions disclosed herein are suitable for delivery to the eye.

In some embodiments, the crystalline forms of Compound 5 described herein may be intended for delivery in a subject's tissues having mucus (e.g., eye, respiratory tract, gastrointestinal tract, genito-urinary tract), which is a viscoelastic and adhesive substance that traps most foreign objects (e.g., microorganisms, particles, dust). For effective drug delivery, compound or particles that are immobilized in the mucus are quickly eliminated by mucus clearance mechanisms; therefore, they are not able to effectively deliver the intended therapeutic effect. In these tissues, for the compound to effective, it must quickly penetrate the mucus and/or avoid mucus clearance mechanisms. Accordingly, modifying mucoadhesive compounds or particles containing compounds with a coating to reduce the mucoadhesiveness, and decreasing the size of the particles of compound may allow for efficient delivery and therapeutic effect.

In some embodiments, the crystalline Form II of N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide is formulated into mucus-penetrating particles or mucus-penetrating nanocrystals (collectively, MPPs) suitable for administration (e.g., topical or inhalation) to tissues of the subject having mucus (e.g., eye, respiratory tract, gastrointestinal tract, genitourinary tract).

Some embodiments, relate to methods of treating and/or preventing a disease associated with abnormal angiogenesis in a subject in need thereof.

Some embodiments relate to methods of treating and/or preventing a disease associated with aberrant signaling of a growth factor signaling pathway in a subject in need thereof.

Some embodiments relate to methods of inhibiting angiogenesis in a subject in need thereof.

Some embodiments relate to methods of inhibiting aberrant signaling of a growth factor signaling pathway in a subject or cell. In certain embodiments, the growth factor is associated with angiogenesis. In certain embodiments, the growth factor is VEGF.

Some embodiments include administering to the subject an effective amount of a compound or pharmaceutical composition disclosed herein. In certain embodiments, the effective amount is a therapeutically effective amount. In certain embodiments, the effective amount is a prophylactically effective amount.

Some embodiments may provide compounds and pharmaceutical compositions disclosed herein, for use in the treatment and/or prevention of a disease associated with abnormal angiogenesis and/or associated with aberrant signaling of a growth factor signaling pathway in a subject in need thereof.

Some embodiments relate to kits comprising a container with a compound or pharmaceutical composition disclosed herein. The kits may include a single dose or multiple doses of the inventive compound, or pharmaceutical compositions thereof. The provided kits may be useful in treating and/or preventing a disease associated with abnormal angiogenesis and/or with aberrant signaling of a growth factor in a subject in need thereof. The kits may also be useful for inhibiting abnormal angiogenesis and/or aberrant signaling of a growth factor signaling pathway in a subject in need thereof. In certain embodiments, the kit further includes instructions for administering the compound, or pharmaceutical composition, to the subject.

Some embodiments may refer to various issued patents, published patent applications, journal articles, and other publications, all of which are incorporated herein by reference.

DETAILED DESCRIPTION

Definitions

Figure 1:
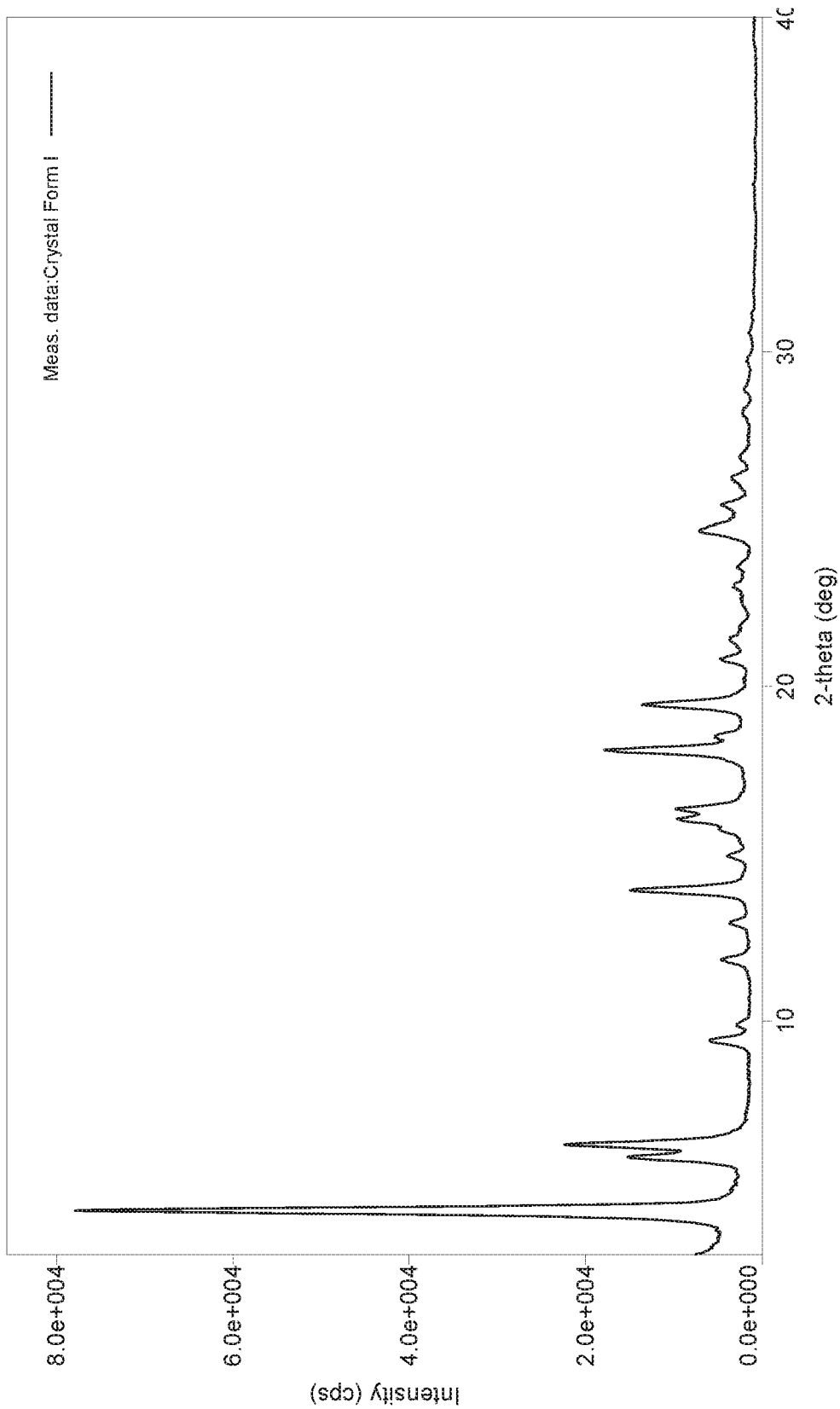
FIG. 1 provides a representative X-Ray Powder Diffraction (XRPD) pattern for crystalline Form I of Compound 5 acquired as described in Example 3.

The following definitions are more general terms used throughout the present application.

As used herein, when referring to X-Ray Powder Diffraction (XRPD) peak positions, "about" means ±0.2, and more preferably ±0.1.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds included herein include those derived from suitable inorganic and organic acids and bases.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. Crystalline Form I and Crystalline Form II of Compound 5 described herein may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5$H_2O$)), and polyhydrates (x is a number greater than 1, e.g., dihydrates (R.2$H_2O$) and hexahydrates (R.6$H_2O$)).

The term "polymorphs" refers to a crystalline or crystal form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female at any stage of development. The animal may be a transgenic animal or genetically engineered animal. In certain embodiments, the subject is non-human animal. In one embodiment, the subject is a human. A "patient" refers to a human subject in need of treatment of a disease.

The terms "administer," "administering," or "administration," as used herein, refers to implanting, absorbing, applying, ingesting, injecting, inhaling, instilling, or otherwise introducing Crystalline Form I and Crystalline Form II of Compound 5, or a pharmaceutical composition thereof, in, to, or on a subject.

As used herein, the terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

As used herein, the terms "condition," "disease," and "disorder" are used interchangeably.

An "effective amount" of a compound described herein refers to an amount sufficient to elicit the desired biological response, i.e., treating a disease or condition. As will be appreciated by those of ordinary skill in this art, the effective amount of Crystalline Form I and Crystalline Form II of Compound 5 described herein may vary depending on such factors as the desired biological endpoint, the pharmacokinetics of the compound and crystalline form, the condition being treated, the mode of administration, and the age and health of the subject. An effective amount encompasses therapeutic and prophylactic treatment.

A "therapeutically effective amount" of Crystalline Form I and Crystalline Form II of Compound 5 described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a "therapeutically effective amount" of a compound or pharmaceutical composition is the amount needed to inhibit angiogenesis in a subject.

A "prophylactically effective amount" of Crystalline Form I and Crystalline Form II of Compound 5 described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "growth factor" refers to a naturally occurring substance (e.g., a protein or a steroid hormone) capable of stimulating cellular growth, proliferation, and cellular differentiation. Growth factors may act as signaling molecules between cells and/or promote cell differentiation and maturation.

As used herein, the term "vascular endothelial growth factor" or "VEGF" refers to a signal protein produced by cells that stimulate vasculogenesis and angiogenesis. VEGFs are a sub-family of growth factors, i.e., the platelet-derived growth factor family of cystine-knot growth factors. VEGFs are important signaling proteins involved in both vasculogenesis and angiogenesis. VEGFs' normal function is to create new blood vessels during embryonic development, new blood vessels after injury, muscle following exercise, and new vessels (collateral circulation) to bypass blocked vessels. When VEGF is overexpressed, it can contribute to a range of diseases, such as proliferative diseases (e.g., cancer) and vascular diseases in the retina of the eye and other parts of the body. VEGFs include a number of proteins from two families that result from alternate splicing of mRNA from a single, 8-exon, VEGF gene. Examples of VEGFs include, but are not limited to, VEGF-related proteins such as placental growth factor (PGF), VEGF-A, VEGF-B, VEGF-C, VEGF-D, VEGF-E, and VEGF-F. The term "VEGF" also encompasses VEGF receptors (VEGFRs), such as VEGFR-1, VEGFR-2 and VEGFR-3. A VEGFR may be membrane-bound (mbVEGFR) or soluble (sVEGFR).

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) pathological proliferation of normally quiescent cells; 2) pathological migration of cells from their normal location (e.g., metastasis of neoplastic cells); 3) pathological expression of proteolytic enzymes such as the matrix metalloproteinases (e.g., collagenases, gelatinases, and elastases); or 4) pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

As used herein, the term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF).

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. A malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

As used herein, the term "cancer" refers to a malignant neoplasm (*Stedman's Medical Dictionary*, 25th ed.; Hensyl ed.; Williams & Wilkins: Philadelphia, 1990).

As used herein, the term "inflammatory disease" or "inflammation" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Examples of inflammatory diseases include, without limitation, autoimmune disorders, systemic lupus erythematosus, psoriasis, cystic fibrosis, rheumatoid arthritis, inflammatory arthritis, Sjogren's syndrome, inflammatory bowel disease, Crohn's disease, ulcerative colitis, pneumonia, respiratory tract inflammation, Adult Respiratory Distress Syndrome (ARDS), asthma, allograft rejection, and vaginitis. Ocular inflammatory diseases include, but are not limited to, allergy of the eye, uveitis (e.g., anterior uveitis, intermediate uveitis, and posterior uveitis), conjunctivitis, panuveitis, cyclitis, scleritis, episcleritis, optic neuritis, retrobulbar optic neuritis, keratitis (e.g., immune keratitis and infectious keratitis), blepharitis, corneal ulcer, conjunctival ulcer and symptoms caused by them, ocular inflammatory diseases caused by ocular disorders, ocular inflammatory diseases caused by a physical injury, post-surgical inflammation, and dry eye (e.g., dry eye syndrome).

As used herein, an "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney).

The term "ocular disease" or "ocular disorder" refers to any eye disease and/or disorder. For example, ocular diseases can be disorders of the eyelid, lacrimal system and orbit, disorders of conjunctiva, disorders of sclera, cornea, iris and ciliary body, disorders of choroid and retina, glaucoma, disorders of optic nerve and visual pathways, occulary inflammatory diseases, or disorders of ocular muscles. Additionally, ocular disease can also refer to discomfort following injury, surgery, or laser treatment. Diseases and disorders of the eye include, but are not limited to, macular degeneration, dry eye syndrome, uveitis, allergic conjunctivitis, glaucoma, and rosacea (of the eye). Dry eye syndrome (DES), otherwise known as keratoconjunctivitis sicca (KCS), keratitis sicca, sicca syndrome, or xerophthalmia, is an eye disease caused by decreased tear production or increased tear film evaporation commonly found in humans and some animals The term "age-related macular degeneration" or "AMD" is an ocular disease which usually affects older adults and results in a loss of vision in the center of the visual field (the macula) because of damage to the retina. It occurs in "dry" and "wet" forms. It is a major cause of blindness and visual impairment in older adults (>50 years). Macular degeneration can make it difficult or impossible to read or recognize faces, although enough peripheral vision remains to allow other activities of daily life. In the dry (nonexudative) form, cellular debris called drusen accumulate between the retina and the choroid, and the retina can become detached. In the wet (exudative) form, which is more severe, blood vessels grow up from the choroid behind the retina, and the retina can also become detached. AMD can be treated with laser coagulation, and with medication that stops and sometimes reverses the growth of blood vessels. AMD begins with characteristic yellow deposits (drusen) in the macula, between the retinal pigment epithelium and the underlying choroid. Most patients with these early changes (referred to as age-related maculopathy) have good vision. Patients with drusen can go on to develop advanced AMD. The risk is considerably higher when the drusen are large and numerous and associated with disturbance in the pigmented cell layer under the macula.

The term "macular edema" refers to the ocular diseases cystoid macular edema (CME) or diabetic macular edema (DME). CME is an ocular disease that affects the central retina or macula of the eye. When this condition is present, multiple cyst-like (cystoid) areas of fluid appear in the macula and cause retinal swelling or edema. CME may accompany a variety of diseases such as retinal vein occlusion, uveitis, and/or diabetes. CME commonly occurs after cataract surgery. DME occurs when blood vessels in the retina of patients with diabetes begin to leak into the macula, the part of the eye responsible for detailed central vision. These leaks cause the macula to thicken and swell, progressively distorting acute vision. While the swelling may not lead to blindness, the effect can cause a severe loss in central vision.

The term "glaucoma" refers to an ocular disease in which the optic nerve is damaged in a characteristic pattern. This can permanently damage vision in the affected eye and lead to blindness if left untreated. It is normally associated with increased fluid pressure in the eye (aqueous humor). The term ocular hypertension is used for patients with consistently raised intraocular pressure (IOP) without any associated optic nerve damage. Conversely, the term normal tension or low tension glaucoma is used for those with optic nerve damage and associated visual field loss but normal or low IOP. The nerve damage involves loss of retinal ganglion cells in a characteristic pattern. There are many different subtypes of glaucoma, but they can all be considered to be a type of optic neuropathy. Raised intraocular pressure (e.g., above 21 mmHg or 2.8 kPa) is the most important and only modifiable risk factor for glaucoma, though some may have high eye pressure for years and never develop damage, while others can develop nerve damage at a relatively low pressure. Untreated glaucoma can lead to permanent damage of the optic nerve and resultant visual field loss, which over time can progress to blindness.

The term "uveitis" refers to an inflammatory disease of the uvea, the vascular layer of the eye sandwiched between the retina and the sclera (white of the eye). The uvea extends toward the front of the eye and consists of the iris, choroid layer and ciliary body. Uveitis includes anterior uveitis, intermediate uveitis, and posterior uveitis. A common type of uveitis is an inflammation of the iris called iritis (anterior uveitis). Uveitis may also occur at the posterior segment of the eye (e.g., at the choroid). Inflammation of the uvea can be recurring and can cause serious problems such as blindness if left untreated, and accounts for 10% of blindness globally. Early diagnosis and treatment are important to prevent the complications of uveitis.

The term "dry eye" or "dry eyes" refers to an ocular disease in which there are insufficient tears to lubricate and nourish the eye. Tears are necessary for maintaining the health of the front surface of the eye and for providing clear vision. Patients with dry eyes either do not produce enough tears or have a poor quality of tears. Dry eye is a common and often chronic problem, particularly in older adults. With each blink of the eyelids, tears are spread across the front surface of the eye, known as the cornea. Tears provide lubrication, reduce the risk of eye infection, wash away foreign matter in the eye, and keep the surface of the eyes smooth and clear. When the normal amount of tear production decreases or tears evaporate too quickly from the eyes, symptoms of dry eye can develop. The most common form of dry eyes is due to an inadequate amount of the water layer of tears. This condition, called keratoconjunctivitis sicca (KCS), is also referred to as "dry eye syndrome." A non-limiting example of dry eye syndrome is Sjögren's syndrome.

The term "diabetic retinopathy" refers to retinopathy (i.e., a disease of the retina) caused by complications of diabetes, which can eventually lead to blindness. Diabetic retinopathy may cause no symptoms, mild vision problems, or even blindness. Diabetic retinopathy is the result of microvascular retinal changes. Hyperglycemia-induced intramural pericyte death and thickening of the basement membrane lead to incompetence of the vascular walls. These damages change the formation of the blood-retinal barrier and also make the retinal blood vessels become more permeable. Small blood vessels, such as those in the eye, are especially vulnerable to poor control over blood sugar. An overaccumulation of glucose and/or fructose damages the tiny blood vessels in the retina. During the initial stage, called "nonproliferative diabetic retinopathy" (NPDR), most patients do not notice any change in their vision. Early changes that are reversible and do not threaten central vision are sometimes termed simplex retinopathy or background retinopathy. As the disease progresses, severe nonproliferative diabetic retinopathy enters an advanced, "proliferative diabetic retinopathy" (PDR) stage when blood vessels proliferate. The lack of oxygen in the retina causes fragile, new, blood vessels to grow along the retina and in the clear, gel-like vitreous humor that fills the inside of the eye, which may result in bleeding, cloudy vision, retina damage, or tractional retinal detachment.

The terms "crystalline" or "substantially crystalline", when used with respect to nanostructures, refer to the fact that the nanostructures typically exhibit long-range ordering across one or more dimensions of the structure. It will be understood by one of skill in the art that the term "long range ordering" will depend on the absolute size of the specific nanostructures, as ordering for a single crystal cannot extend beyond the boundaries of the crystal. In this case, "long-range ordering" will mean substantial order across at least the majority of the dimension of the nanostructure. The terms "crystalline" or "substantially crystalline" as used herein are intended to also encompass structures comprising various defects, stacking faults, atomic substitutions, and the like, as long as the structure exhibits substantial long range ordering (e.g., order over at least about 80% of the length of at least one axis of the nanostructure or its core). In addition, it will be appreciated that the interface between a core and the outside of a nanostructure or between a core and an adjacent shell or between a shell and a second adjacent shell may contain non-crystalline regions and may even be amorphous. This does not prevent the nanostructure from being crystalline or substantially crystalline as defined herein. The term "monocrystalline" when used with respect to a nanostructure indicates that the nanostructure is substantially crystalline and comprises substantially a single crystal. When used with respect to a nanostructure heterostructure comprising a core and one or more shells, "monocrystalline" indicates that the core is substantially crystalline and comprises substantially a single crystal. When not used with respect to a nanostructure, the term "monocrystalline" refers to materials that are composed of substantially a single crystallite of substantially the same size and orientation.

"Nanocrystal" is a nanostructure that is substantially monocrystalline. A nanocrystal thus has at least one region or characteristic dimension with a dimension of less than about 1000 nm, e.g., less than about 300 nm, less than about 200 nm, less than about 100 nm, or less than about 50 nm. Typically, the region or characteristic dimension will be along the smallest axis of the structure. Optionally, a nanocrystal can comprise one or more surface ligands (e.g., surfactants). The nanocrystal is optionally substantially single crystal in structure (a "single crystal nanostructure" or a "monocrystalline nanostructure"). The term "nanocrystal" is intended to encompass substantially monocrystalline nanostructures comprising various defects, stacking faults, atomic substitutions, and the like, as well as substantially monocrystalline nanostructures without such defects, faults, or substitutions. In the case of nanocrystal heterostructures comprising a core and one or more shells, the core of the nanocrystal is typically substantially monocrystalline, but the shell(s) need not be.

As used herein, the terms "pharmaceutical composition" and "formulation" are used interchangeably.

As used herein, the terms "pharmaceutical agent" and "drug" are used interchangeably.

DETAILED DESCRIPTION

Some embodiments include crystalline Form I and crystalline Form II of a compound having the formula

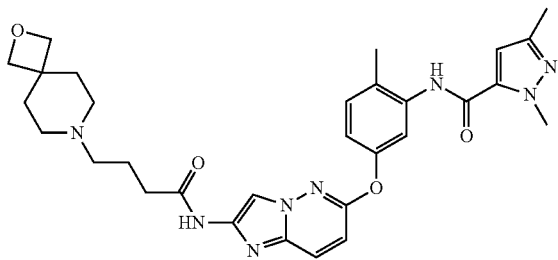 [SMILES: Cc1cc(C(=O)Nc2cc(Oc3ccc4nc(NC(=O)CCCN5CCC6(CC5)COC6)cn4n3)ccc2C)n(C)n1]

A chemical name for this compound is N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, also referred to herein as Compound 5.

Some embodiments relate to a compound having the formula

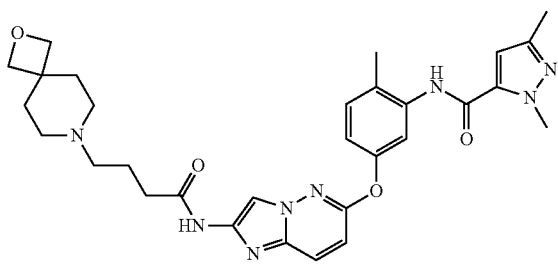 [SMILES: Cc1cc(C(=O)Nc2cc(Oc3ccc4nc(NC(=O)CCCN5CCC6(CC5)COC6)cn4n3)ccc2C)n(C)n1]

in crystalline Form II. In certain embodiments, the crystalline form is crystalline Form II having an X-ray powder diffraction (XRPD) pattern with peaks at about 3.42, 4.59, and 13.71±0.2 degrees two-theta, or 25.78, 19.23, and 6.46±0.2 Å in d-spacing. In further embodiments, crystalline Form II further has XRPD peaks at about 17.13 and 17.82±0.2 degrees two-theta, or 5.17 and 4.97±0.2 Å in d-spacing. In further embodiments, crystalline Form II further has XRPD peaks at about 5.08, 7.36, 7.94, 10.20, 12.91, 14.72, and 25.64±0.2 degrees two-theta, or 17.40, 12.01, 11.12, 8.67, 6.85, 6.01, and 3.47±0.2 Å in d-spacing.

Some embodiments relate to a compound having the formula

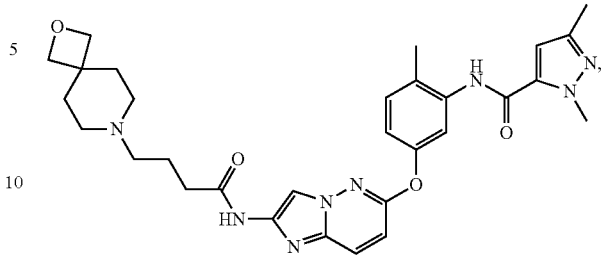

in crystalline Form II having an X-ray powder diffraction (XRPD) pattern with peaks at about 3.42, 4.59, 5.08, 7.36, 7.94, 10.20, 12.91, 13.71, 14.72, 17.13, 17.82, and 25.64±0.2 degrees two-theta, or 25.78, 19.23, 17.40, 12.01, 11.12, 8.67, 6.85, 6.46, 6.01, 5.17, 4.97, 3.47±0.2 Å in d-spacing.

Some embodiments relate to N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide in crystalline Form II. In certain embodiments, the crystalline form is crystalline Form II having an X-ray powder diffraction (XRPD) pattern with peaks at about 3.42, 4.59, and 13.71±0.2 degrees two-theta, or 25.78, 19.23, and 6.46±0.2 Å in d-spacing. In further embodiments, crystalline Form II further has XRPD peaks at about 17.13 and 17.82±0.2 degrees two-theta, or 5.17 and 4.97±0.2 Å in d-spacing. In further embodiments, crystalline Form II further has XRPD peaks at about 5.08, 7.36, 7.94, 10.20, 12.91, 14.72, and 25.64±0.2 degrees two-theta, or 17.40, 12.01, 11.12, 8.67, 6.85, 6.01, and 3.47±0.2 Å in d-spacing.

Some embodiments relate to Crystalline Form II of a compound having the formula

Figure 4:
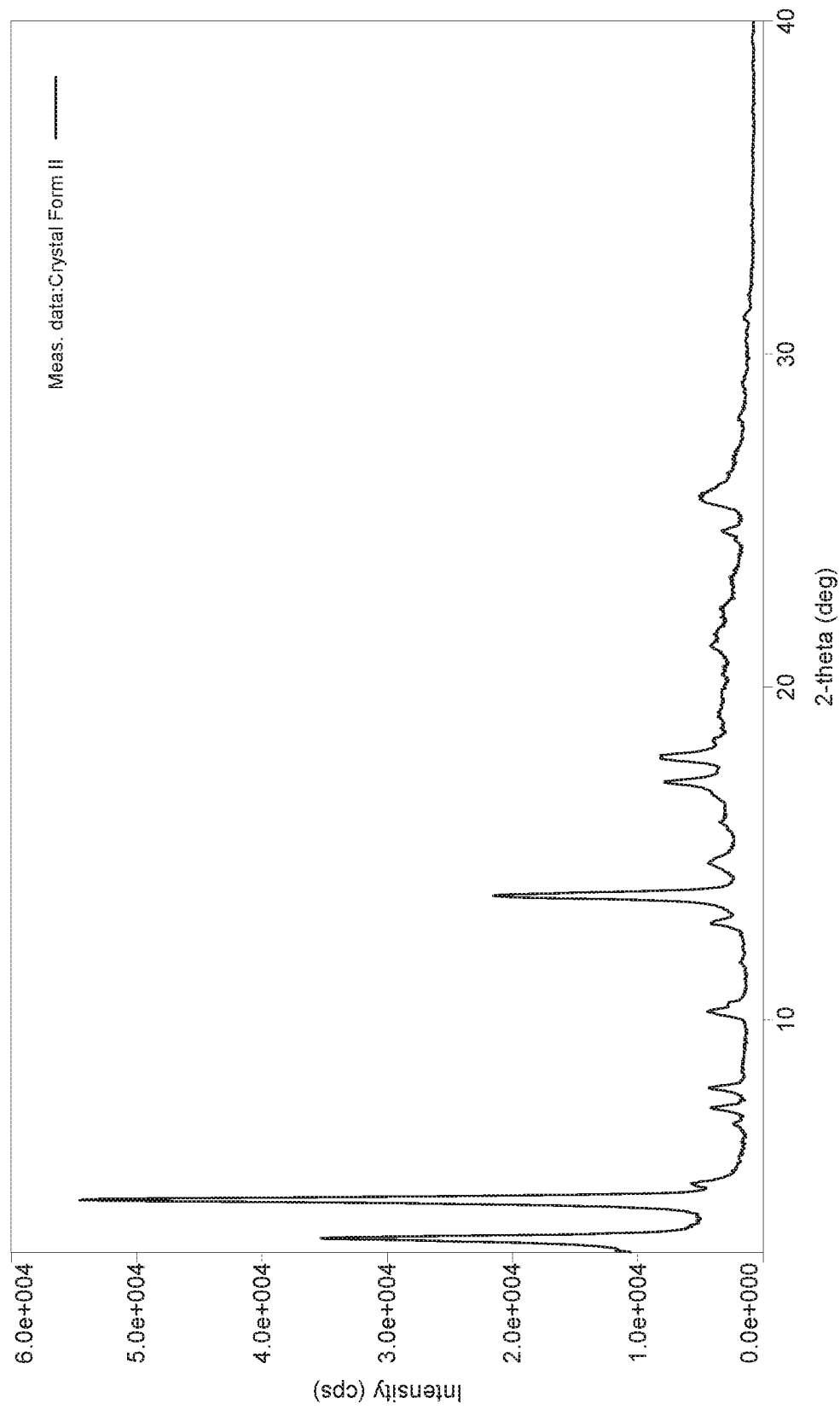
FIG. 4 provides a representative XRPD pattern for crystalline Form II of Compound 5 acquired as described in Example 3.

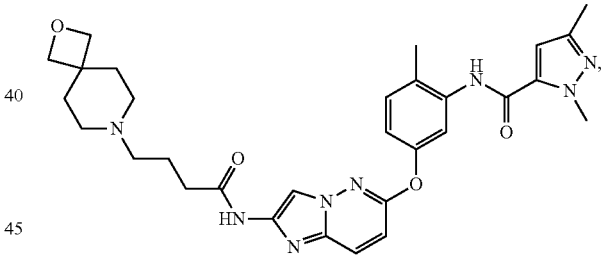

having the X-ray powder diffraction pattern as shown in FIG. 4.

Some embodiments relate to a compound having the formula

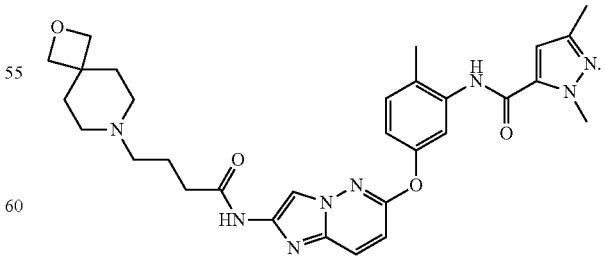

in crystalline Form I. In certain embodiments, the crystalline form is crystalline Form I having an X-ray powder diffraction (XRPD) pattern with peaks at about 4.31, 6.30, 13.90, 18.06, and 19.40±0.2 degrees two-theta, or 20.49, 14.02, 6.37, 4.91, and 4.57±0.2 Å in d-spacing. In further embodiments, crystalline Form I further has XRPD peaks at about 5.90, 16.01, and 16.25±0.2 degrees two-theta, or 14.96, 5.53, and 5.45±0.2 Å in d-spacing. In further embodiments, crystalline Form I further has XRPD peaks at about 9.37, 9.89, 11.80, 12.91, 14.84, 20.79, and 24.58±0.2 degrees two-theta, or 9.44, 8.94, 7.50, 6.85, 5.97, 4.27, and 3.62±0.2 Å in d-spacing.

Some embodiments relate to a compound having the formula

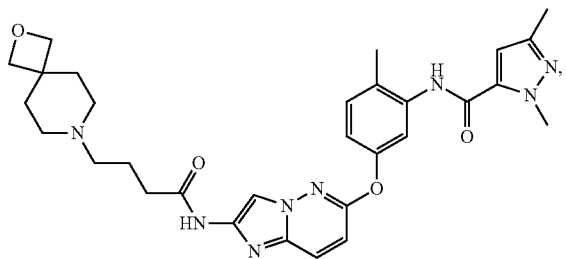

in crystalline Form I having an X-ray powder diffraction (XRPD) pattern with peaks at about 4.31, 5.90, 6.30, 9.37, 9.89, 11.80, 12.91, 13.90, 14.84, 16.01, 16.25, 18.06, 19.40, 20.79, and 24.58±0.2 degrees two-theta, or 20.49, 14.96, 14.02, 9.44, 8.94, 7.50, 6.85, 6.37, 5.97, 5.53, 5.45, 4.91, 4.57, 4.27, and 3.62±0.2 Å in d-spacing.

Some embodiments relate to N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide in crystalline Form I. In certain embodiments, the crystalline form is crystalline Form I having an X-ray powder diffraction (XRPD) pattern with peaks at about 4.31, 6.30, 13.90, 18.06, and 19.40±0.2 degrees two-theta, or 20.49, 14.02, 6.37, 4.91, and 4.57±0.2 Å in d-spacing. In further embodiments, crystalline Form I further has XRPD peaks at about 5.90, 16.01, and 16.25±0.2 degrees two-theta, or 14.96, 5.53, and 5.45±0.2 Å in d-spacing. In further embodiments, crystalline Form I further has XRPD peaks at about 9.37, 9.89, 11.80, 12.91, 14.84, 20.79, and 24.58±0.2 degrees two-theta, or 9.44, 8.94, 7.50, 6.85, 5.97, 4.27, and 3.62±0.2 Å in d-spacing.

Some embodiments relate to Crystalline Form I of a compound having the formula

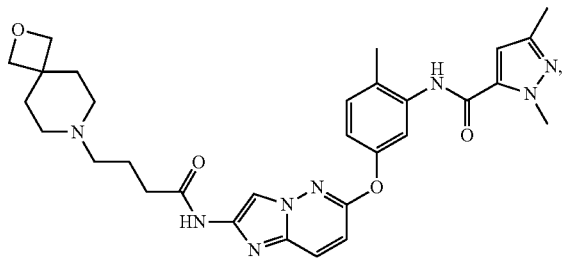

having the X-ray powder diffraction pattern as shown in FIG. 1.

In certain embodiments, the crystalline forms of Compound 5 are monocrystalline. In certain embodiments, the crystalline forms of Compound 5 are polycrystalline.

Compound 5 is disclosed in co-pending PCT International Application No. PCT/US2014/040231. The form of Compound 5 resulting from the synthesis and isolation steps described in the Examples of that application is an amorphous compound.

In some embodiments, the crystalline forms of Compound 5 described herein may be intended for delivery in a subject's tissues having mucus (e.g., eye, respiratory tract, gastrointestinal tract, genito-urinary tract), which is a viscoelastic and adhesive substance that traps most foreign objects (e.g., microorganisms, particles, dust). For effective drug delivery, compound or particles that are immobilized in the mucus are quickly eliminated by mucus clearance mechanisms; therefore, they are not able to effectively deliver the intended therapeutic effect. In these tissues, for the compound to effective, it must quickly penetrate the mucus and/or avoid mucus clearance mechanisms. Accordingly, modifying mucoadhesive compounds or particles containing compounds with a coating to reduce the mucoadhesiveness, and decreasing the size of the particles of compound may allow for efficient delivery and therapeutic effect.

In some embodiments, crystalline Form II of N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide is formulated into mucus-penetrating particles or mucus-penetrating nanocrystals (collectively, MPPs) suitable for administration (e.g., topical or inhalation) to tissues of the subject having mucus (e.g., eye, respiratory tract, gastrointestinal tract, genito-urinary tract).

Crystalline Form II, or mucus-penetrating particles or mucus-penetrating nanocrystals thereof, may be suitable for being processed into mucus-penetrating pharmaceutical compositions (e.g., particles or crystals). In certain embodiments, the compounds disclosed herein are suitable for milling (e.g., nano-milling). In certain embodiments, the compounds disclosed herein are suitable for precipitation (e.g., microprecipitation, nanoprecipitation, crystallization, or controlled crystallization). In certain embodiments, the compounds disclosed herein are suitable for emulsification. In certain embodiments, the compounds disclosed herein are suitable for freeze-drying.

Crystalline Form I or Crystalline Form II of N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide may be useful in treating and/or preventing a disease (e.g., a disease associated with abnormal angiogenesis and/or aberrant signaling of a growth factor signaling pathway (e.g., VEGF)) in a subject in need thereof. The compounds disclosed herein may also be useful in inhibiting abnormal angiogenesis and/or aberrant signaling of a growth factor pathway in a subject and/or cell.

Pharmaceutical Compositions and Administration

Some embodiments include pharmaceutical compositions comprising Crystalline Form I of N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, and optionally a pharmaceutically acceptable carrier or excipient. In certain embodiments, the pharmaceutical composition comprises crystalline Form II of N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, and optionally a pharmaceutically acceptable carrier or excipient.

In some embodiments, crystalline Form I or crystalline Form II of N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating and/or preventing a disease. In certain embodiments, the effective amount is an amount effective for treating a disease. In certain embodiments, the effective amount is an amount effective for treating and/or preventing a disease associated with aberrant signaling of a growth factor. In certain embodiments, the effective amount is an amount effective for treating a disease associated with aberrant signaling of a growth factor. In certain embodiments, the effective amount is an amount effective for treating and/or preventing a disease associated with aberrant signaling of vascular endothelial growth factor (VEGF). In certain embodiments, the effective amount is an amount effective for treating a disease associated with aberrant signaling of vascular endothelial growth factor (VEGF). In certain embodiments, the effective amount is an amount effective for treating and/or preventing a disease associated with abnormal angiogenesis, such as cancer, benign neoplasm, atherosclerosis, hypertension, inflammatory disease, rheumatoid arthritis, macular degeneration, choroidal neovascularization, retinal neovascularization, and diabetic retinopathy. In certain embodiments, the effective amount is an amount effective to treat cancer (e.g., an ocular cancer). In certain embodiments, the effective amount is an amount effective to treat macular degeneration.

An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In some embodiments, an effective amount of a compound may inhibit abnormal angiogenesis and/or aberrant signaling of a growth factor by at least about 10%, at least about 20%, at least about 30%, at least about 40%, at least about 50%, at least about 60%, at least about 70%, at least about 80%, or at least about 90%. An effective amount of a compound may inhibit abnormal angiogenesis and/or aberrant signaling of a growth factor by less than about 90%, less than about 80%, less than about 70%, less than about 60%, less than about 50%, less than about 40%, less than about 30%, less than about 20%, or less than about 10%. Combinations of the ranges described herein (e.g., at least 20% and less than 50%) are also within the scope of the disclosure. In certain embodiments, an effective amount of a compound inhibits abnormal angiogenesis and/or aberrant signaling of a growth factor by a percentage or a range of percentage described herein, compared to normal angiogenesis and/or signaling.

Pharmaceutical compositions described herein can be prepared by any method known in the art of pharmacology. In general, such preparatory methods include the steps of bringing Crystalline Form I or Crystalline Form II of Compound 5 described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient, crystalline Form I and crystalline Form II of Compound 5, is generally equal to the dosage of the active ingredient which would be administered to a subject and/or a convenient fraction of such a dosage such as, for example, one-half or one-third of such a dosage.

In some embodiments, relative amounts of the active ingredient, the pharmaceutically acceptable excipient, and/or any additional ingredients in a pharmaceutical composition will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Crystalline Form I or crystalline Form II of Compound 5, and pharmaceutical compositions thereof provided herein, can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by solutions, suspensions, drops, powders, ointments, gels, and/or creams), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, topical administration, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition may be suitable for topical administration to the eye of a subject.

In some embodiments, the pharmaceutical compositions are suitable for topical administration. In some embodiments, the pharmaceutical compositions are suitable for injection. In one embodiment, the pharmaceutical compositions comprising crystalline Form I or crystalline Form II of Compound 5 are suitable for delivery to the eye. In some embodiments, pharmaceutical compositions comprising crystalline Form I or crystalline Form II of Compound 5 may be suitable for oral administration. In some embodiments, the pharmaceutical compositions comprising crystalline Form I or crystalline Form II of Compound 5 may be suitable for inhalation.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers, and mixtures thereof. Besides inert diluents, the oral compositions can include adjuvants such as wetting agents, emulsifying and suspending agents, sweetening, flavoring, and perfuming agents.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent. The injectable formulations can be sterilized, for example, by filtration through a bacterial-retaining filter, or by incorporating sterilizing agents in the form of sterile solid compositions that can be dissolved or dispersed in sterile water or other sterile injectable medium prior to use.

Compositions for rectal or vaginal administration are typically suppositories that can be prepared by mixing an active ingredient as described herein with suitable non-irritating excipients or carriers such as cocoa butter, polyethylene glycol, or a suppository wax that are solid at ambient temperature but liquid at body temperature and therefore melt in the rectum or vaginal cavity and release the active ingredient.

Solid dosage forms for oral administration include capsules, gelatin capsules, tablets, pills, powders, and granules. In such solid dosage forms, the active ingredient (e.g., crystalline Form I or crystalline Form II of Compound 5) is mixed with at least one inert, pharmaceutically acceptable excipient or carrier known in the art, including without limitation fillers or extenders, binders, humectants, disintegrating agents, solution retarding agents, absorption accelerators, wetting agents, absorbents, and lubricants, and mixtures thereof. In the case of capsules, tablets, and pills, the dosage form may include a buffering agent.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art.

Dosage forms for topical and/or transdermal administration of crystalline Form I or crystalline Form II of Compound 5 may include solutions, suspensions, ointments, pastes, creams, lotions, gels, powders, sprays, inhalants, and/or patches. Generally, the active ingredient is admixed under sterile conditions with a pharmaceutically acceptable carrier or excipient and/or any needed preservatives and/or buffers as can be required. Additionally, some embodiments contemplate the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Alternatively or additionally, conventional syringes can be used in the classical mantoux method of intradermal administration. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as solutions, suspensions, liniments, lotions, oil-in-water and/or water-in-oil emulsions such as creams, ointments, and/or pastes. Topically administrable formulations may, for example, comprise from about 1% to about 10% (w/w) of pharmaceutical agent (e.g., crystalline Form I or crystalline Form II of Compound 5), although the concentration of the pharmaceutical agent can be as high as the solubility limit of the pharmaceutical agent in the solvent. Formulations for topical administration may further comprise one or more of the additional ingredients described herein. In one embodiment, pharmaceutical compositions suitable for topical administration are solutions or suspensions. In another embodiment, the solution or suspension is in the form of eye drops.

A pharmaceutical composition can be prepared, packaged, and/or sold in a formulation suitable for pulmonary administration via the buccal cavity. Such a formulation may comprise dry particles that comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein.

A pharmaceutical composition can be prepared, packaged, and/or sold in a formulation for ophthalmic administration, such as solutions, suspensions, ointments, or gels. Such formulations may, for example, be in the form of eye drops including, for example, a 0.1/1.0% (w/w) solution and/or suspension of the active ingredient (e.g., crystalline Form I or crystalline Form II of Compound 5) in an aqueous or oily liquid carrier or excipient. Such drops may further comprise buffering agents, salts, and/or one or more other of the additional ingredients described herein. Other opthalmically-administrable formulations that are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions that are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The exact amount of crystalline Form I or crystalline Form II of Compound 5, N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of crystalline Form I or crystalline Form II of Compound 5 for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that crystalline Form I or crystalline Form II of Compound 5, N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, or a pharmaceutical composition thereof, as described herein, can be administered in combination with one or more additional pharmaceutical agents (e.g., therapeutically and/or prophylactically active agents). Crystalline Form I or crystalline Form II of Compound 5, or compositions thereof, can be administered in combination with additional pharmaceutical agents that improve their activity, bioavailability, reduce and/or modify their metabolism, inhibit their excretion, and/or modify their distribution within the body of a subject. It will also be appreciated that the therapy employed may achieve a desired effect for the same disorder, and/or it may achieve different effects.

Crystalline Form I or crystalline Form II of Compound 5, N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, or a pharmaceutical composition thereof, can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

In certain embodiments, crystalline Form I or crystalline Form II of Compound 5, N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, pharmaceutical compositions thereof, and methods may be useful for applications in the eye, such as treating and/or preventing an ocular disease (e.g., macular degeneration, dry eye syndrome, diabetic macular edema, cystoid macular edema, uveitis, allergic conjunctivitis, glaucoma, and rosacea). In certain embodiments, the pharmaceutical compositions can be topically administered to the eye of a subject. Topical pharmaceutical compositions administered to the eye are advantageous over pharmaceutical compositions that are administered to the eye by injection or orally.

In certain embodiments, crystalline Form II of Compound 5 is formulated as a mucus-penetrating particles. Methods for preparing mucus-penetrating particles have been described in, for example, U.S. Patent Publication Nos. 2008/0166414, 2010/0215580, 2013/0164343, 2013/0236556, 2013/0316001, 2013/0316006, 2013/0316009, and 2013/0323179, each of which is herein incorporated by reference in its entirety. Some embodiments relate to a pharmaceutical composition of crystalline Form II of Compound 5, N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, wherein said pharmaceutical composition comprises mucus-penetrating particles of crystalline Form II and a pharmaceutically acceptable excipient.

Methods of Treatment and Uses

A range of diseases may result when the body of a subject loses control over angiogenesis, i.e., new blood vessels grow abnormally (i.e., excessively or insufficiently) or grow as a result of a tumor. Excessive angiogenesis is often observed in subjects with diseases such as proliferative diseases (e.g., cancers, benign neoplasms, inflammatory diseases, autoimmune diseases) and ocular diseases, especially with cancer, diabetic retinopathy, macular degeneration, rheumatoid arthritis, and psoriasis. In these diseases, new blood vessels feed abnormal tissues and/or destroy normal tissues. Excessive angiogenesis may occur when there are abnormal amounts of angiogenic growth factors present, overwhelming the effects of natural angiogenesis inhibitors. Therefore, inhibiting new blood vessel growth may be useful to treat diseases associated with excessive angiogenesis. Insufficient angiogenesis is typically observed in subjects with a disease such as coronary artery disease, stroke, or chronic wounds. In these diseases, blood vessel growth is inadequate, and circulation is not properly restored, which may lead to tissue death.

VEGFs have been found to play a major role in angiogenesis, for example, by increasing the number of capillaries in a given network. In vitro studies have demonstrated that bovine capillary endothelial cells proliferated and showed signs of tube structures upon stimulation with VEGF. Upregulation of VEGF is a major component of the physiological response to exercise and its role in angiogenesis is suspected to be a possible treatment in vascular injuries. In vitro studies have showed that VEGFs are a potent stimulator of angiogenesis because, among other things, in the presence of this growth factor, plated endothelial cells will proliferate and migrate, eventually forming tube structures resembling capillaries. VEGFs may cause a massive signaling cascade in endothelial cells. Binding to VEGF receptor-2 starts a tyrosine kinase signaling cascade that stimulates the production of factors that variously stimulate vessel permeability, proliferation/survival, migration, and finally differentiation into mature blood vessels. Mechanically, VEGF is upregulated with muscle contractions as a result of increased blood flow to affected areas. The increased flow also causes a large increase in the mRNA production of VEGF receptors 1 and 2. The increase in receptor production indicates that muscle contractions could cause upregulation of the signaling cascade relating to angiogenesis.

Some embodiments provide methods of treating and/or preventing a disease associated with abnormal angiogenesis in a subject in need thereof. In certain embodiments, the disease being treated and/or prevented by the inventive methods is associated with excessive and/or pathological angiogenesis.

Some embodiments provide methods of treating and/or preventing a disease associated with aberrant signaling of a growth factor in a subject in need thereof. In certain embodiments, the disease is associated with excessive signaling of the growth factor. In certain embodiments, the disease being treated and/or prevented by the inventive methods is associated with aberrant signaling of VEGF. In certain embodiments, the disease is associated with excessive or aberrant signaling of VEGF-A, VEGF-B, VEGF-C, VEGF-D, VEGF-F, and/or placental growth factor (PGF).

In certain embodiments, the disease being treated and/or prevented by the inventive methods is a proliferative disease. All types of proliferative diseases described herein may be treated and/or prevented by the inventive methods. In certain embodiments, the disease being treated and/or prevented by the inventive methods is cancer. All types of cancer described herein may be treated and/or prevented by the inventive methods. In certain embodiments, the cancer is an ocular cancer. In certain embodiments, the ocular cancer is retinoblastoma, medulloepithelioma, uveal melanoma, ciliary body melanoma, or primary intraocular lymphoma. In certain embodiments, the disease being treated and/or prevented by the inventive methods is a benign neoplasm. All types of benign neoplasm described herein may be treated and/or prevented by the inventive methods. In certain embodiments, the benign neoplasm is an ocular benign neoplasm. In certain embodiments, the benign neoplasm is orbital dermoid cysts.

In certain embodiments, the disease being treated and/or prevented by the inventive methods is an inflammatory disease. All types of inflammatory diseases described herein may be treated and/or prevented by the inventive methods. In certain embodiments, the inflammatory disease is an ocular inflammatory disease. In certain embodiments, the ocular inflammatory disease is post-surgical inflammation. In certain embodiments, the disease being treated and/or prevented by the inventive methods is an autoimmune disease. All types of autoimmune diseases described herein may be treated and/or prevented by the inventive methods. In certain embodiments, the autoimmune disease is rheumatoid arthritis. In certain embodiments, the disease being treated and/or prevented by the inventive methods is diabetes. In certain embodiments, the disease is type 1 diabetes. In certain embodiments, the disease is type 2 diabetes. In certain embodiments, the disease is gestational diabetes.

The disease being treated and/or prevented by the inventive methods is an ocular disease. In some embodiments, the ocular disease being treated and/or prevented by the inventive methods is an anterior ocular disease that occurs at the anterior portion or "front" of the eye of a subject. The anterior portion of the eye includes the cornea, iris, conjunctiva, tear film, corneal epithelium, anterior chamber, lens, ciliary body, ciliary zonule, posterior chamber, retina, macula, sclera, an optic nerve, choroid, and vitreous chamber. In certain embodiments, the anterior ocular disease being treated and/or prevented by the inventive methods is allergy, post-surgical inflammation, uveitis, an infection (e.g., a viral, bacterial, or fungal infection), aphakia, pseudophakia, astigmatism, blepharospasm, cataract, a conjunctival disease, conjunctivitis, a corneal disease, corneal oedema, meibomiam gland disease, corneal transplant surgery, corneal ulcer, dry eye (e.g., dry eye syndrome), an eyelid disease, a lacrimal apparatus disease, lacrimal duct obstruction, laser induced exudation, myopia, presbyopia, pterygium, pupil disorders, corneal neovascularization, a refractive disorder, strabismus, or glaucoma. In some embodiments, the ocular disease being treated and/or prevented by the inventive methods is a posterior ocular disease that occurs at the posterior portion or "back" of the eye. The posterior portion of the eye includes the choroid, sclera, vitreous humor, vitreous chamber, retina, macula, optic nerve, and blood vessels and nerves which vascularize or innervate a posterior ocular region or site. In certain embodiments, the posterior ocular disease being treated and/or prevented by the inventive methods is intraocular melanoma, acute macular neuroretinopathy, an exudative eye disease, Behcet's disease, exudative retinopathy, macular oedema, retinopathy of prematurity, an epiretmal membrane disorder, choroidal neovascularization, uveitis, diabetic uveitis, histoplasmosis, an infection (e.g., a viral, bacterial, or fungal infection), macular degeneration (e.g., acute macular degeneration and age-related macular degeneration (AMD, such as non-exudative age-related macular degeneration and exudative age-related macular degeneration)), edema (e.g., macular edema, such as cystoid macular edema (CME) and diabetic macular edema (DME)), multifocal choroiditis, ocular trauma which affects a posterior ocular site or location, ocular cancer, a retinal disorder (e.g., central retinal vein occlusion), diabetic retinopathy (e.g., proliferative diabetic retinopathy and nonproliferative diabetic retinopathy), proliferative vitreoretinopathy (PVR), retinal arterial occlusive disease, retinal detachment, uveitic retinal disease, sympathetic opthalmia, Vogt Koyanagi-Harada (VKH) syndrome, uveal diffusion, a posterior ocular condition caused by or influenced by an ocular laser treatment, a posterior ocular condition caused by or influenced by a photodynamic therapy, photocoagulation, radiation retinopathy, an epiretinal membrane disorder, branch retinal vein occlusion, anterior ischemic optic neuropathy, non-retinopathy diabetic retinal dysfunction, retinitis pigmentosa, retinoblastoma, or glaucoma. In certain embodiments, the ocular disease being prevented and/or treated by the inventive methods is macular degeneration. In certain embodiments, the ocular disease is age-related macular degeneration (AMD). In certain embodiments, the ocular disease is glaucoma. In certain embodiments, the ocular disease is diabetic retinopathy. In certain embodiments, the ocular disease is retinoblastoma. In certain embodiments, the ocular disease is edema. In certain embodiments, the ocular disease is cystoid macular edema (CME). In certain embodiments, the ocular disease is diabetic macular edema (DME). In certain embodiments, the ocular disease is an ocular inflammatory disease. In certain embodiments, the ocular disease is post-surgical inflammation. In certain embodiments, the ocular disease is uveitis (e.g., anterior uveitis, intermediate uveitis, and post uveitis). In certain embodiments, the ocular disease is blepharitis. In certain embodiments, the ocular disease is panuveitis. In certain embodiments, the ocular disease is scleritis. In certain embodiments, the ocular disease is dry eye. In certain embodiments, the ocular disease is Sjögren's syndrome. In certain embodiments, the ocular disease is an eye surgery.

Some embodiments relate to methods of inhibiting the aberrant signaling of a growth factor signaling pathway (e.g., VEGF) in a subject or cell.

Some embodiments provide methods of inhibiting abnormal or pathological angiogenesis in a subject in need thereof.

Some embodiments relate to a method of treating an ocular disease comprising administering to a subject in need thereof a therapeutically effective amount of crystalline Form I of Compound 5 as described herein, or a pharmaceutical composition thereof. In one aspect, the ocular disease is retinopathy. In another embodiment, the ocular disease is age-related macular degeneration (AMD). In another embodiment, the ocular disease is corneal neovascularization. In yet another embodiment, the ocular disease is diabetic macular edema (DME). In a further embodiment, the ocular disease is cystoid macular edema (CME). In yet another embodiment, the ocular disease is retinal vein occlusion (RVO).

Some embodiments relate to a method of treating an ocular disease comprising administering to a subject in need thereof a therapeutically effective amount of crystalline Form II of Compound 5, N-(5-((2-(4-(2-oxa-7-azaspiro[3.5] nonan-7-yl)butanamido)imidazo[1,2-b]pyridazin-6-yl)oxy)-2-methylphenyl)-1,3-dimethyl-1H-pyrazole-5-carboxamide, as described herein, or a pharmaceutical composition thereof. In one aspect, the ocular disease is retinopathy. In another embodiment, the ocular disease is age-related macular degeneration (AMD). In another embodiment, the ocular disease is corneal neovascularization. In yet another embodiment, the ocular disease is diabetic macular edema (DME). In a further embodiment, the ocular disease is cystoid macular edema (CME). In yet another embodiment, the ocular disease is retinal vein occlusion (RVO).

In certain embodiments, the subject described herein is a human. In certain embodiments, the subject is an animal. The animal may be of either sex and may be at any stage of development. In certain embodiments, the subject is a mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate.

In certain embodiments, the animal is a genetically engineered animal. In certain embodiments, the animal is a transgenic animal.

In certain embodiments, the cell described herein is in vivo. In certain embodiments, the cell is in vitro. In certain embodiments, the cell is ex vitro.

Some embodiments include administering to a subject in need thereof an effective amount of crystalline Form I or crystalline Form II of Compound 5, N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, or pharmaceutical compositions thereof, as described herein.

Some embodiments provide crystalline Form I or crystalline Form II of Compound 5, N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, or pharmaceutical compositions thereof, for use in the treatment and/or prevention of a disease described herein in a subject in need thereof.

Some embodiments provide crystalline Form I or crystalline Form II of Compound 5, N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, or pharmaceutical compositions thereof, for use in the inhibition of abnormal angiogenesis in a subject in need thereof.

Some embodiments provide crystalline Form I or crystalline Form II of Compound 5, N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide, or pharmaceutical compositions thereof, for use in the inhibition of aberrant signaling of a growth factor in a subject or cell in need thereof.

EXAMPLES

In order that some embodiments herein may be more fully understood, the following examples are set forth. The synthetic and biological examples described in this application are offered to illustrate the compounds, pharmaceutical compositions, and methods provided herein and are not to be construed in any way as limiting their scope.

Example 1

Preparation of Compound 5 (N-(5-((2-(4-(2-oxa-7-azaspiro[3.5]nonan-7-yl)butanamido)imidazo[1,2-b]pyridazin-6-yl)oxy)-2-methylphenyl)-1,3-dimethyl-1H-pyrazole-5-carboxamide)

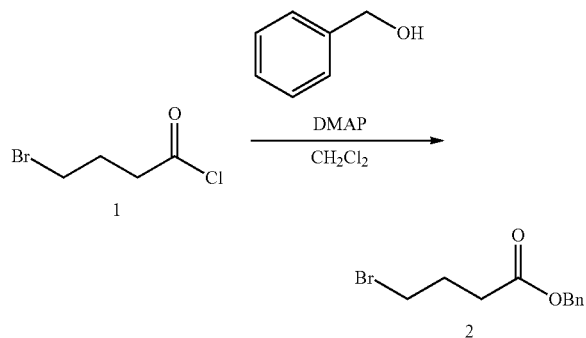

Benzyl alcohol (3.1 mL, 30 mmol) was added to a solution of Compound 1 (3.47 mL, 30 mmol) and 4-dimethylaminopyridine (732 mg, 6 mmol) in dichloromethane (100 mL). The reaction was stirred for 2 hours at room temperature then quenched with 1 M HCl (100 mL). The organic phase was washed once more with 1 M HCl (100 mL), dried over MgSO$_4$, filtered, dried by rotary evaporation and was dried under vacuum to yield Compound 2 as a colorless oil (6.29 g, 24.5 mmol, 82%).

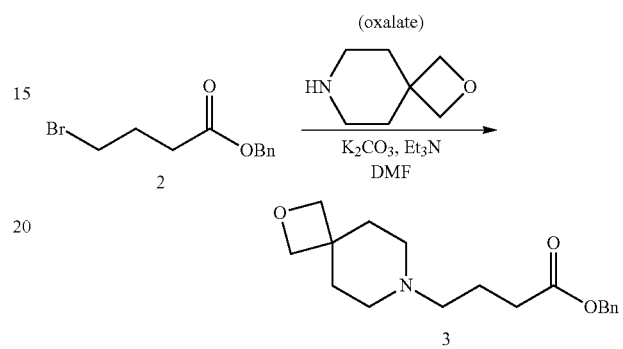

A suspension of 2-oxa-7-azaspiro[3.5]nonane hemioxalate (3.77 g, 17.38 mmol), potassium carbonate (4.8 g, 34.76 mmol), and triethylamine (4.85 mL, 34.76 mmol) was stirred in dry dimethylformamide (20 mL) for 10 minutes. A solution of Compound 2 (4.47 g, 17.38 mmol) in dry dimethylformamide (5 mL) was added and the reaction stirred at 60° C. for 1 hour. Solvent was azeotroped with toluene by rotary evaporator. Crude residue was dissolved in methanol and purified by ISCO flash chromatography to yield Compound 3 as a colorless oil (3.53 g, 11.7 mmol, 67%).

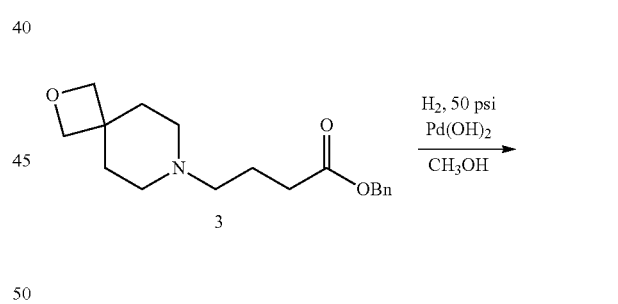

A Parr hydrogenation vessel was charged with a methanol solution (100 mL) of Compound 3 (3.53 g, 11.7 mmol) and Pd(OH)$_2$/C (375 mg, 10% wt). Contents were agitated at 50 psi of hydrogen for 4 hours. Slurry was filtered through a CELITE pad and the pad washed with methanol (50 mL). The filtrate was concentrated by rotary evaporator and the residue co-evaporated with dichloromethane (100 mL) twice. The product, Compound 4, was a viscous yellow syrup that was used in the next reaction without purification.

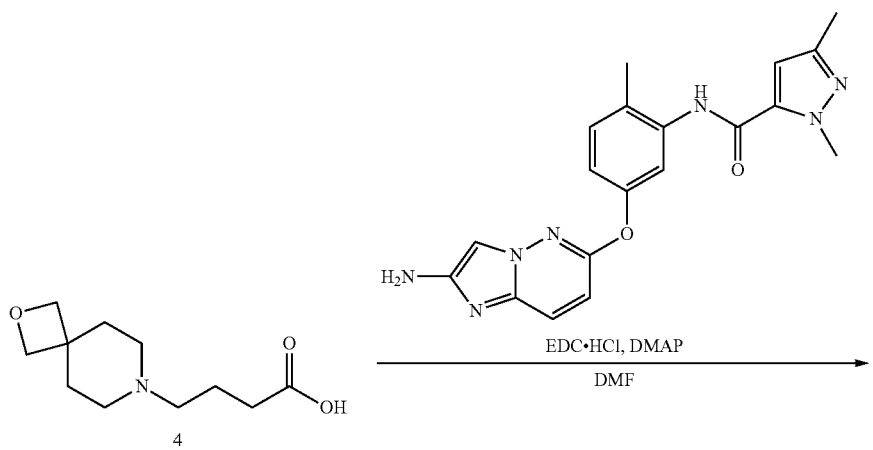

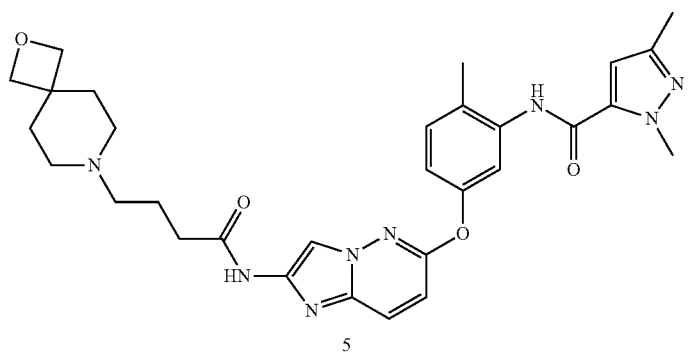

N-(5-((2-aminoimidazo[1,2-b]pyridazin-6-yl)oxy)-2-methylphenyl)-1,3-dimethyl-1H-pyrazole-5-carboxamide (2.1 g, 5.57 mmol), Compound 4 (1.54 g, 7.24 mmol), and 4-dimethylaminopyridine (680 mg, 5.57 mmol) were dissolved in dry dimethylformamide (20 mL). N-(3-Dimethylaminopropyl)-N'-ethylcarbodiimide hydrochloride (1.6 g, 8.36 mmol) was added and the reaction stirred at room temperature for 21 hours. Solvent was azeotroped with toluene by rotary evaporator (4×50 mL). Remaining orange-brown syrup was diluted in methanol and aged in the freezer overnight. Compound 5 crystallized from the solution and was filtered, then washed with methanol and hexanes. Solids were dried under high vacuum to yield 750 mg white solid (1.31 mmol, 24%).

The foregoing synthesis produced Crystalline Form I of Compound 5.

Example 2

Preparation of Crystalline Form II of Compound 5

Crystalline Form II was prepared by crystallization of Crystalline Form I of Compound 5 in acetonitrile/water (90:10) co-solvent. The results of the crystallization experiments are summarized in Table 1.

TABLE 1

Summary of crystallization to produce Crystalline Form II

| Sample Vial | Amount Dissolved (mg) | Volume of Co-solvent added (µL) | Initial Concentration (mg/mL) | Amount Recovered (mg) | Recovery Yield by mass |
|---|---|---|---|---|---|
| 1 | 47.03 | 500 | 94.06 | 37.44 | 79.61% |
| 2 | 49.47 | 500 | 98.94 | 38.45 | 77.72% |
| 3 | 52.79 | 500 | 105.58 | 36.35 | 68.86% |

In one instance, approximately 50 mg of Crystalline Form I of Compound 5 was deposited into each of three 6-mL scintillation vials with screw-tops, henceforth referred to as the working vials. To each working vial was added a 7×2 mm magnetic stir bar, while the co-solvent was separately being heated to 50° C. in separate 20-mL scintillation vials on an IKA RCT Basic hot plate. Five hundred microliters of co-solvent were transferred to each of the three working vials and the vials were transferred into a heating plate equipped with a magnetic stirrer. The vials were stirred at 400 RPM, then the temperature of the heating plate was raised to 65° C. and Crystalline Form I of Compound 5 was allowed to dissolve. Following dissolution, the heating and stirring were halted, and the stir bars were removed using metallic tweezers. The working vials were transported to a clear area and were allowed to equilibrate to ambient temperature (approximately 22° C.) overnight.

After a 24-hr incubation period, crystals were present in all three working vials. The mother liquors were decanted using a pipette and each of the working vials was covered by a single KIMWIPE sheet, then the working vials were dried under high vacuum overnight. The solid material was analyzed by XRPD the next day, which showed a powder pattern that is unique compared to Crystalline Form I, thereby indicating that Crystalline Form II was successfully obtained.

Example 3

Characterization of Crystalline Form I and Form II of Compound 5

General Procedure to Acquire X-Ray Powder Diffraction (XRPD) Patterns.

A Rigaku MiniFlex 600 equipped with a Cu X-ray tube (Cu/Kα=1.54059 Å) was used. Approximately 5 mg of compound was deposited onto a Rigaku 906165 Flush, Si510 sample plate. Using a spatula and firm pressure, the sample was spread thinly and evenly on the surface of the plate. The XRPD pattern was collected from 3°-40° two-theta at a step size of 0.02° two-theta and a speed of 5.0° two-theta degrees per minute. The source was kept at 40 kV with a 15 mA current running through it for the duration of the experiment.

General Procedure to Obtain Differential Scanning Calorimetry (DSC) Thermogram.

TA Instruments Q1000 was used to obtain DSC data. Approximately 0.5-1.0 mg of compound was loaded in hermetic pans that were subsequently crimped and then manually punctured once in the middle using a 23-gauge needle. Samples were heated from ambient temperature to 300° C. at 5° C./minute.

General Procedure to Obtain Thermogravimetric Analysis (TGA) Thermogram.

TA Instruments Q5000 was used to obtain TGA data. An aluminum pan was loaded with ~5-10 mg of sample, then heated from ambient temperature to 300° C. at 10° C./minute.

Example 3A

Characterization of Crystalline Form I of Compound 5

An XRPD pattern for Crystalline Form I of Compound 5 was acquired using the method described above, and the resulting XRPD pattern of crystalline Form I is shown in FIG. 1. A tabulation of the peaks in two-theta and the corresponding d-spacing values comprised in the XRPD pattern are listed in Table 2.

TABLE 2

XRPD peak listing of Crystalline Form I.

| Peak No. | Position ± 0.2° [2 theta] | d-spacing ± 0.2 [Å] | Relative Intensity [%] |
|---|---|---|---|
| 1 | 4.31 | 20.49 | 100.00 |
| 2 | 5.90 | 14.96 | 16.54 |
| 3 | 6.30 | 14.02 | 25.15 |
| 4 | 9.37 | 9.44 | 5.95 |
| 5 | 9.89 | 8.94 | 2.33 |
| 6 | 11.80 | 7.50 | 3.26 |
| 7 | 12.91 | 6.85 | 1.87 |
| 8 | 13.90 | 6.37 | 17.06 |
| 9 | 14.84 | 5.97 | 1.55 |
| 10 | 16.01 | 5.53 | 13.23 |

TABLE 2-continued

XRPD peak listing of Crystalline Form I.

| Peak No. | Position ± 0.2° [2 theta] | d-spacing ± 0.2 [Å] | Relative Intensity [%] |
|---|---|---|---|
| 11 | 16.25 | 5.45 | 8.30 |
| 12 | 18.06 | 4.91 | 20.80 |
| 13 | 18.48 | 4.80 | 4.20 |
| 14 | 19.40 | 4.57 | 13.53 |
| 15 | 20.79 | 4.27 | 2.36 |
| 16 | 21.42 | 4.15 | 1.77 |
| 17 | 22.95 | 3.87 | 2.07 |
| 18 | 24.58 | 3.62 | 9.43 |
| 19 | 25.39 | 3.51 | 3.49 |
| 20 | 26.19 | 3.40 | 2.71 |
| 21 | 26.83 | 3.32 | 1.19 |
| 22 | 28.15 | 3.17 | 1.33 |
| 23 | 28.80 | 3.10 | 1.21 |
| 24 | 29.72 | 3.00 | 0.77 |

Figure 2:
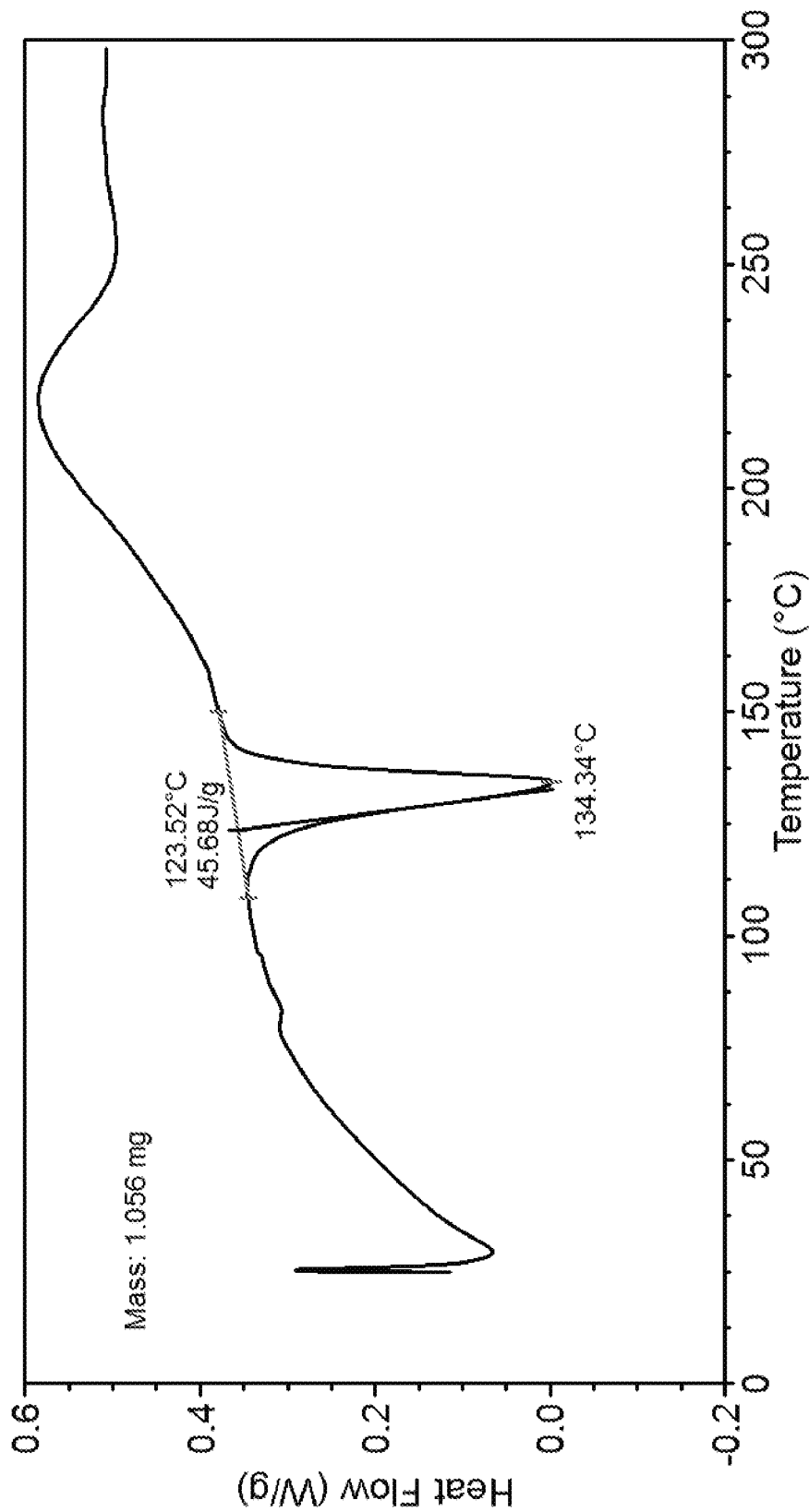
FIG. 2 shows a Differential Scanning calorimetry (DSC) thermogram for crystalline Form I of Compound 5 obtained as described in Example 3.

A DSC trace of Crystalline Form I of Compound 5 was obtained using the method described above, and the resulting DSC thermogram is shown in FIG. 2, which exhibits an endothermic event at 134.34° C.

Figure 3:
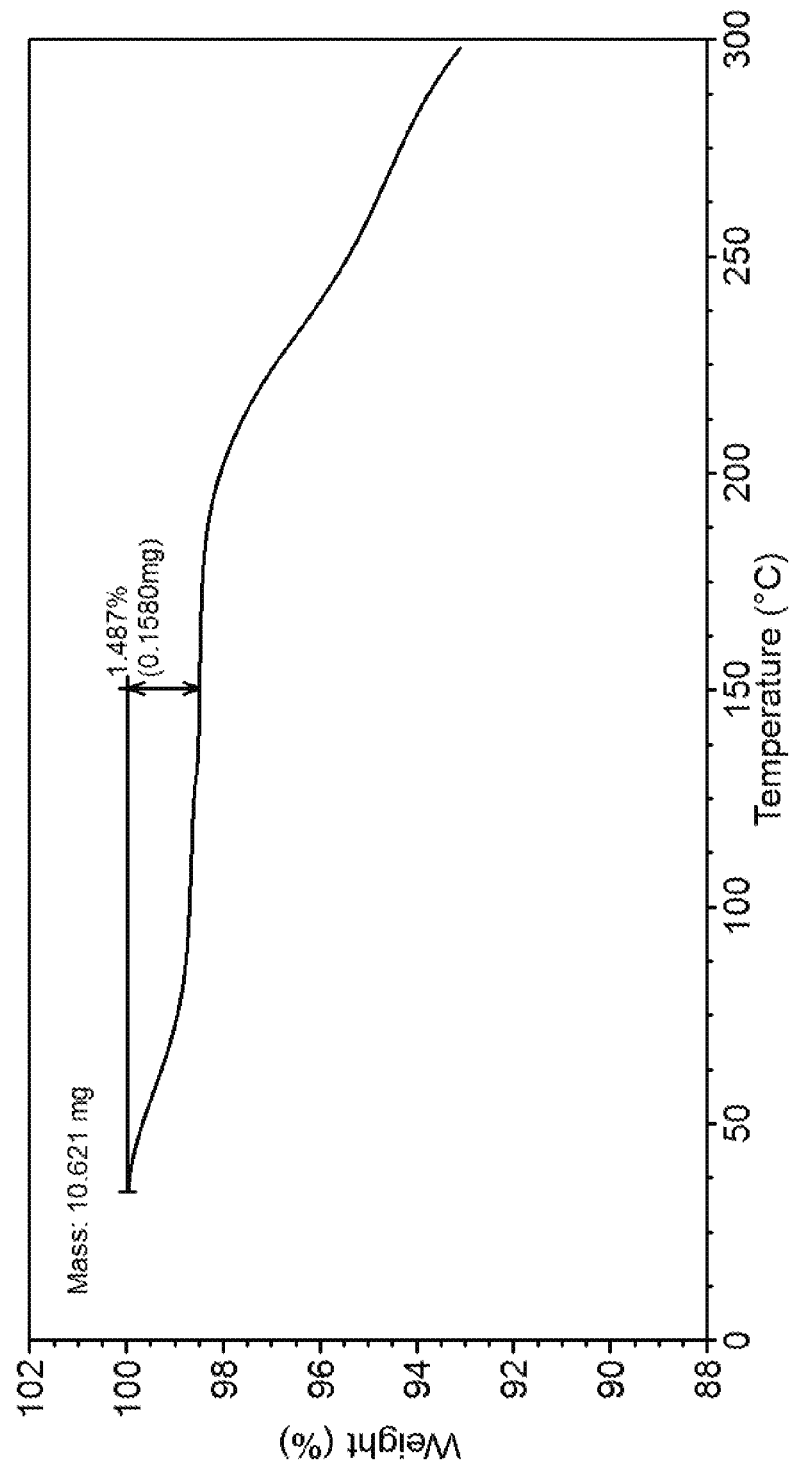
FIG. 3 shows a Thermogravimetric Analysis (TGA) thermogram for crystalline Form I of Compound 5 obtained as described in Example 3.

A TGA thermogram of Crystalline Form I of Compound 5 was obtained using the method described above, and the resulting TGA thermogram is shown in FIG. 3. FIG. 3 shows that the TGA thermogram of Crystalline Form I exhibits an apparent mass loss of ~1.5%.

Example 3B

Characterization of Crystalline Form II of Compound 5

An XRPD pattern for Crystalline Form II of Compound 5 was acquired using the method described above, and the resulting XRPD pattern of Crystalline Form II is shown in FIG. 4. A tabulation of the peaks in two-theta and the corresponding d-spacing values comprised in the XRPD pattern are listed in Table 3.

TABLE 3

XRPD peak listing for Crystalline Form II.

| Peak No. | Position ± 0.2° [2-theta] | d-spacing ± 0.2 [Å] | Relative Intensity [%] |
|---|---|---|---|
| 1 | 3.42 | 25.78 | 63.32 |
| 2 | 4.59 | 19.23 | 100.00 |
| 3 | 5.08 | 17.40 | 4.71 |
| 4 | 7.36 | 12.01 | 5.67 |
| 5 | 7.94 | 11.12 | 6.20 |
| 6 | 10.20 | 8.67 | 7.62 |
| 7 | 12.91 | 6.85 | 4.67 |
| 8 | 13.71 | 6.46 | 44.59 |
| 9 | 14.72 | 6.01 | 6.09 |
| 10 | 17.13 | 5.17 | 12.86 |
| 11 | 17.82 | 4.97 | 14.62 |
| 12 | 21.23 | 4.18 | 8.42 |
| 13 | 22.38 | 3.97 | 1.37 |
| 14 | 24.71 | 3.60 | 2.72 |
| 15 | 25.64 | 3.47 | 22.29 |
| 16 | 27.02 | 3.30 | 1.45 |
| 17 | 34.68 | 2.58 | 1.73 |

Figure 5:
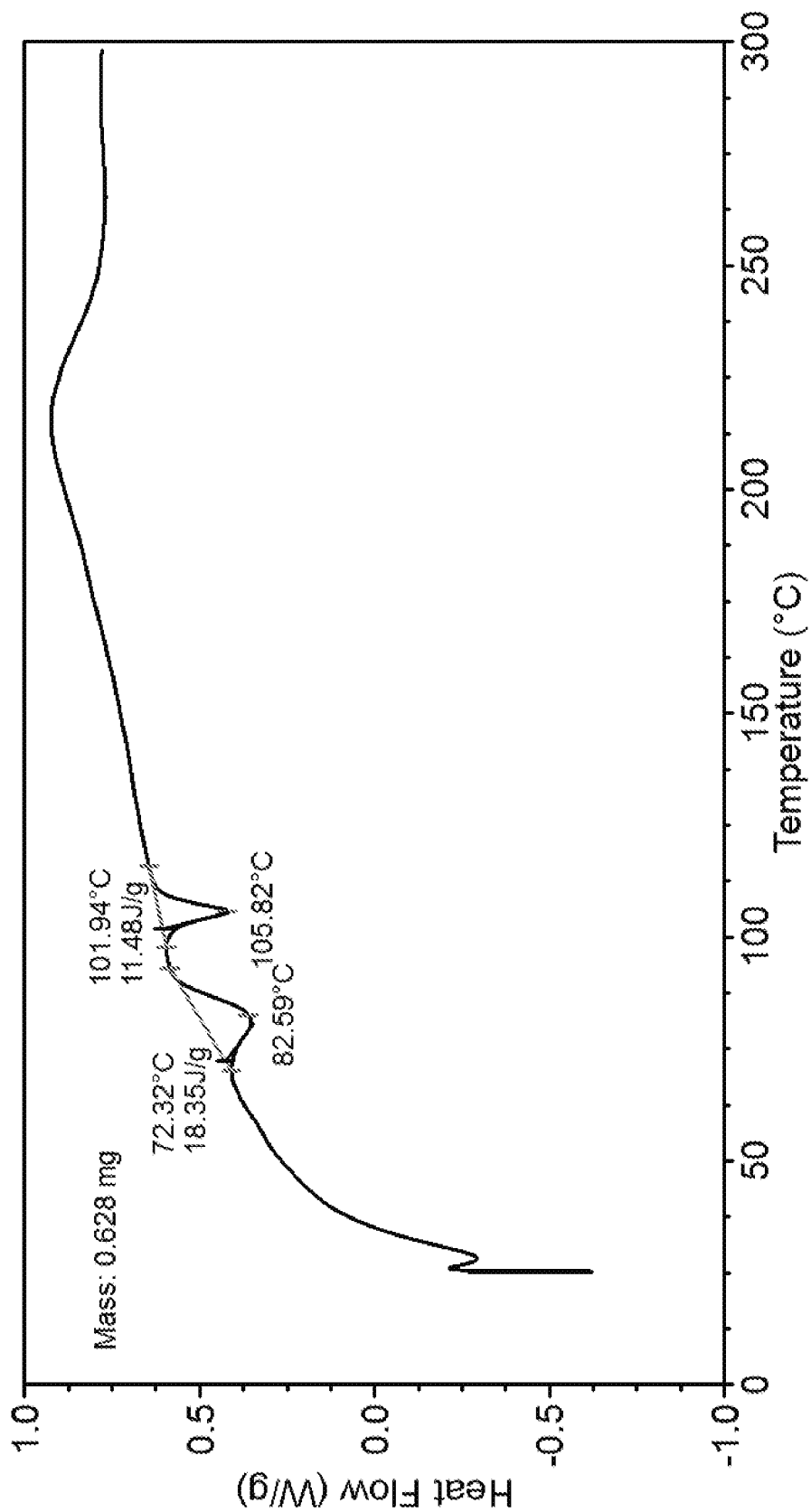
FIG. 5 shows a Differential Scanning calorimetry (DSC) thermogram for crystalline Form II of Compound 5 obtained as described in Example 3.

A DSC trace of Crystalline Form II of Compound 5 was obtained using the method described above, and the resulting DSC thermogram is shown in FIG. 5, which exhibits thermal events at 82.59° C. and 105.82° C.

Figure 6:
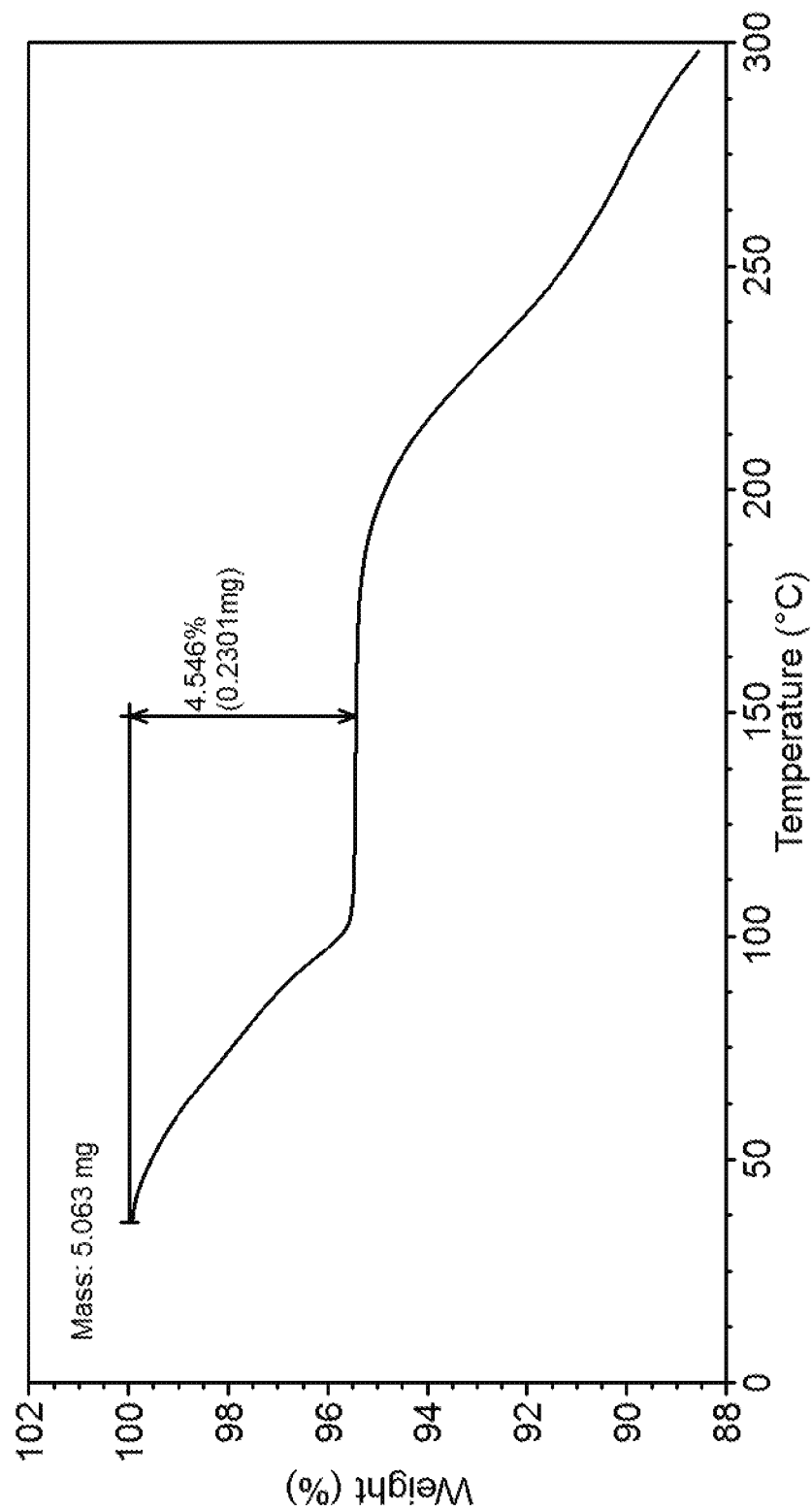
FIG. 6 shows a Thermogravimetric Analysis (TGA) thermogram for crystalline Form II of Compound 5 obtained as described in Example 3

A TGA thermogram of Crystalline Form I of Compound 5 was obtained using the method described above, and the resulting TGA thermogram is shown in FIG. 6. FIG. 6 shows that the TGA thermogram of Crystalline Form II exhibits an apparent mass loss of 4.5%, suggesting that this form is possibly a hydrate.

Example 4

Determination of Thermodynamic Aqueous Solubility

The thermodynamic solubility values of Compound 5 using Crystalline Forms I and II as starting forms were determined in water. In one vial, 10 mg of Crystalline Form I of Compound 5 and 1 mL of water were stirred at ambient temperature for 24 hours at 400 RPM. In a separate vial, 10 mg of Crystalline Form II of Compound 5 was suspended in 1 mL of water, and then the suspension was stirred at ambient temperature for 48 hours at 200 RPM. The equilibrated solids were then separated by dispensing 500 µL of the suspension into a 1.5-mL centrifuge tube, and then centrifuged for 5 minutes at 13,200 RPM using an Eppendorf 5415D centrifuge. As much of the supernatant as possible was decanted using a Pasteur pipette and dispensed into a new 1.5-mL centrifuge tube. The samples were again centrifuged for 5 minutes at 13,200 RPM using the same instrument. The Compound 5 content and pH values of the supernatant were determined by HPLC and pH meter, respectively. The pH of the supernatant was determined to be 9.16. In addition, XRPD analysis of the equilibrated solids revealed that Crystalline Form I converted to amorphous during the time period of the solubility measurement, while Crystalline Form II was stable under similar experimental conditions. The results of the solubility determination are summarized in Table 4.

TABLE 4

Aqueous thermodynamic solubility of Crystalline Form I and Crystalline Form II at ambient temperature (ca. 22° C.)

| Starting Form | Equilibrated form in suspension | Solubility in Water (µg/mL) |
|---|---|---|
| I | Amorphous | 27.76 |
| II | II | 15.76 |

Example 5

Wet Milling of Crystalline Forms I and II of Compound 5 to Produce Nanocrystals General Milling Procedure.

Crystalline Forms of Compound 5 were wet-milled in the presence of stabilizers that enable the preparation of mucus-penetrating particles (MPP) or nanocrystals. The same milling process was employed for all samples. Milling media, specifically 0.5 mL bulk volume of 1-mm ceria-stabilized zirconium oxide beads, was added to a glass vial. Approximately 25 mg of Compound 5 Crystalline Form I or Crystalline Form II and 0.475 mL of milling solution, as specified in each example, were then added to the vial yielding a slurry of 5% Compound 5. A magnetic stir bar was used to agitate the beads, stirring at approximately 500 rpm.

Example 5A

Effects of Milling on Crystalline Form I & Particle Stability

Neat Crystalline Form I of Compound 5 synthesized according to Example 1 was wet-milled in the presence of PLURONIC® F127 (also known as Poloxamer 407) or polyvinyl alcohol with an average MW of 31 kDa and average hydrolysis of 88% (PVA), and a buffer. The details of the wet-milling are listed in Table 5.

TABLE 5

Summary of Compound 5 samples that were produced after milling Form I.

| Starting Form | Sample Number | Milling Solution Stabilizer* | Buffer | Milling Time (days) | Particle Size (nm) |
|---|---|---|---|---|---|
| Form I | Sample 1A | 5% F127 | PBS# | 3 | 203 |
| Form I | Sample 1B | 5% F127 | Borate** | 3 | 207 |
| Form I | Sample 2 | 5% PVA | PBS# | 5 | 550 |

Figure 7:
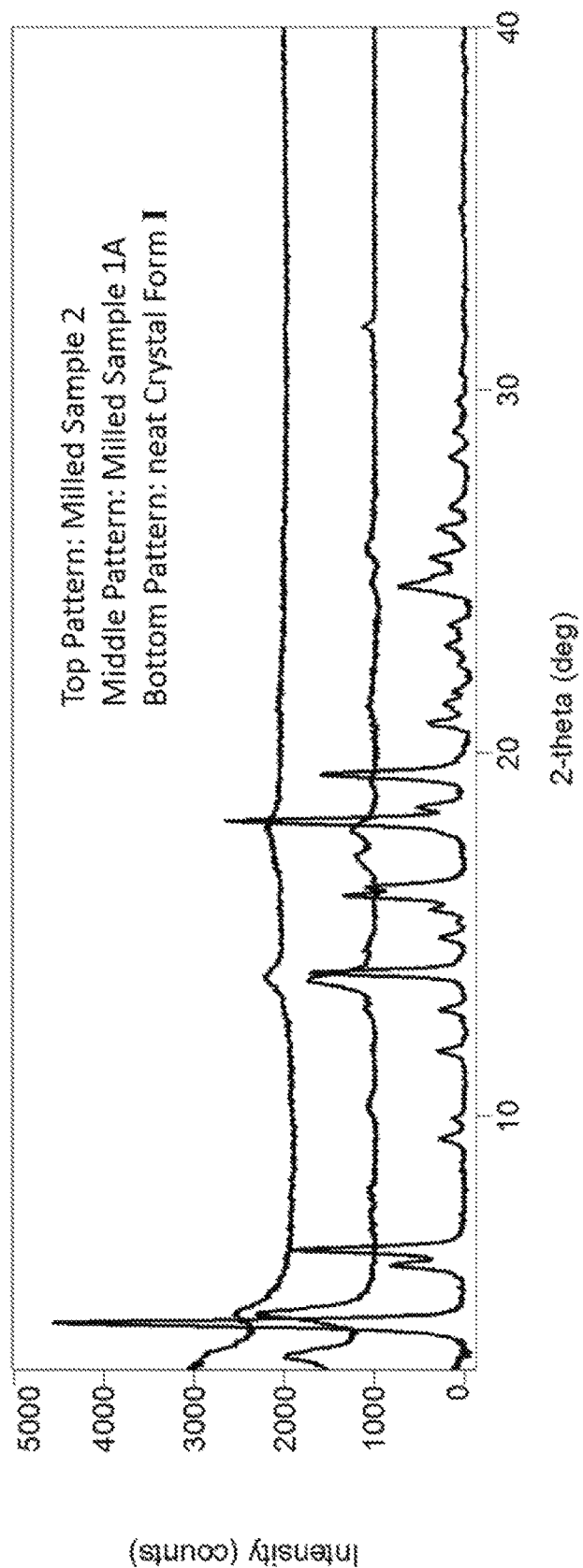
FIG. 7 shows XRPD patterns acquired as described in Example 3 for neat Crystalline Form I of Compound 5, and two milled samples of Crystalline Form I, Sample 1A and Sample 2, obtained as described in Example 5A. These results show that Crystalline Form I of Compound 5 was not stable to the milling process used.

*Stabilizer percentages are the final percentages in the milling slurry.
PBS (pH 7.1) indicates the usage of 0.0067M ($PO_4^{3-}$) phosphate buffered saline
**Borate (pH 8) buffer contained 20 mM borate buffer and 0.7% NaCl for tonicity XRPD patterns for two of the milled samples, Sample 1A and Sample 2, compared to neat Crystalline Form I are shown in FIG. 7. While particle size reduction was achieved to varying degrees, these results demonstrate that Crystalline Form I of Compound 5 was not stable to the milling process under these conditions. Loss of crystallinity and possible form change to amorphous and Crystalline Form II occurred during milling.

Particle size stability was also investigated. Sample 2, which had been milled with PVA, was highly aggregated as evidenced by the large particle size (550 nm) measured by dynamic light scattering (DLS) despite the small particle size observed with scanning electron microscopy (SEM; data not shown). The two samples milled with F127, Samples 1A and 1B, achieved particle sizes below 300 nm and were monitored over 7 weeks at room temperature (RT). The results are shown in Table 6. Substantial size change occurred in both cases. These data further show formulation as a nanocrystal using a method known to produce MPP by wet milling Crystalline Form I of Compound 5 does not lead to a formulation with appropriate physical stability.

TABLE 6

Particle size stability of Compound 5 nanocrystals stored at ambient temperature

| Sample | Initial Size | Size after ~7 weeks at RT | % Increase in Particle Size |
|---|---|---|---|
| 5% Compound 5 nanocrystals in PBS | Sample 1A | 203 nm | 326 nm | 61% |
| 5% Compound 5 nanocrystals in Borate Buffer | Sample 1B | 207 nm | 402 nm | 94% |

Example 5B

Effects of Milling on Crystalline Form II & Particle Stability

Neat Crystalline Form II of Compound 5 prepared in accordance with Example 2 was wet-milled the presence of PLURONIC® F127 (also known as Poloxamer 407) and a buffer. The details of the wet-milling are listed in Table 7.

TABLE 7

Summary of Compound 5 milling procedure for a sample milled from Crystalline Form II.

| Starting Form | Sample | Milling Solution Stabilizer* | Buffer | Milling Time (days) | Particle Size (nm) |
|---|---|---|---|---|---|
| Form II | Sample A | 5% F127 | Borate# | 3 | 220 |

Figure 8:
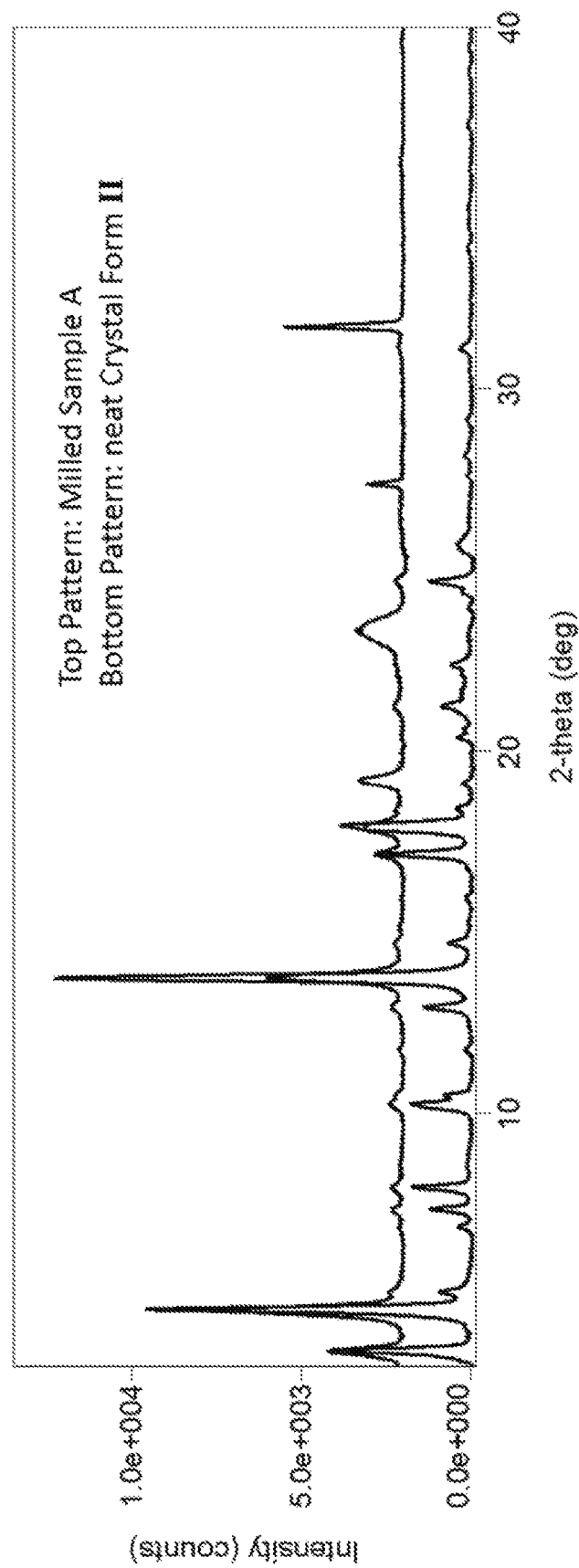
FIG. 8 shows XRPD patterns acquired as described in Example 3 for neat Crystalline Form II of Compound 5 and Milled Sample A nanocrystals of Crystalline Form II obtained as described in Example 5B.

*Stabilizer percentage is the final percentage in the milling slurry
Borate (pH 8) buffer contained 20 mM borate buffer and 0.7% NaCl for tonicity Approximately 100 μL of Sample A was transferred directly onto the surface of the sample XRPD holder, then was allowed to air dry. Its XRPD pattern was then acquired and the data demonstrate that Crystalline Form II of Compound 5 was stable to the milling process under these conditions. XRPD patterns for neat Crystalline Form II and the Milled Sample A nanocrystals are shown in FIG. 8.

Particle size stability was also investigated. Here two formulations were examined: the original Milled Sample A at 5% Crystalline Form II was monitored and a 10× dilution in 20 mM borate buffer (pH 8) with 0.7% NaCl for tonicity was performed yielding a second sample at 0.5% Crystalline Form II. The results are shown in Table 8. While these samples showed a modest increase in size over time, they were significantly more physically stable than the samples obtained by milling of Crystalline Form I.

TABLE 8

Particle size stability of Compound 5 nanocrystals stored at ambient temperature

|  | Sample | Initial Size | Size after ~4 weeks at RT | % Increase in Size |
|---|---|---|---|---|
| 5% Crystalline Form II Nanocrystals | Sample A | 220 nm | 255 nm | 16% |
| 0.5% Crystalline Form II Nanocrystals | Sample B | 220 nm | 259 nm | 18% |

Wet milling Crystalline Form II of Compound 5 to produce nanocrystals may be desired over wet milling Crystalline Form I due to better physical stability in both crystal form and particle size with Crystalline Form II of Compound 5. The results indicate that for formulations or compositions comprising Compound 5 in the form of nanocrystals made by wet-milling, such as formulations comprising mucus-penetrating particles of Compound 5.

Example 6

Back of the Eye Drug Exposure in Mini-Pigs after Topical Instillation of an MPP Comprising Crystalline Form II of Compound 5

A pharmacokinetic (PK) study of the crystalline Form II of Compound 5 formulated as a mucus-penetrating particle (MPP) in accordance with Example 5B was performed in order to demonstrate that topical instillation of MPP formulations of these compounds results in drug exposure at the back of the eye. The formulation used in this study was 2% Compound 5 Form II and 2% PLUROINC® F127 in PBS (0.0067 M ($PO_4^3$) phosphate buffered saline). The study design is shown in Table 9.

TABLE 9

Study design for PK evaluation of Compound 5, Form II MPP

| Group | Test Article | Number of Animals (n/time point) | Dose Volume | Frequency/ Duration | Terminal Time Points (hours) |
|---|---|---|---|---|---|
| 1 | 5, Form II MPP, 2.0% | 3 | 35 μL | BID/5 days | 0.5 |
| 2 | 5, Form II MPP, 2.0% | 3 | 35 μL | BID/5 days | 1 |
| 3 | 5, Form II MPP, 2.0% | 3 | 35 μL | BID/5 days | 2 |
| 4 | 5, Form II MPP, 2.0% | 3 | 35 μL | BID/5 days | 4 |

BID = twice a day

Female Gottingen mini-pigs were used in these studies. Animals received a single topical ocular dose twice daily, approximately 12 hours apart (±1 hour), for 4 consecutive days; on the fifth day animals received a single topical ocular dose in the a.m. only for a total of 9 doses over the study duration.

All animals were euthanized with sodium pentobarbital and blood (approximately 10 mL) collected via cardiac puncture into tubes containing $K_2EDTA$. Samples were maintained on wet ice, in a chilled cryorack, or stored at approximately 5° C. until centrifuged to obtain plasma. Plasma was harvested and placed on dry ice prior to storage at approximately −70° C. until analyzed. Eyes were enucleated, flash frozen in liquid nitrogen for 15 to 20 seconds and stored at approximately −70° C. for at least 2 hours. Within approximately 3 days, the frozen matrices were collected as right and analyzed.

Figure 9:
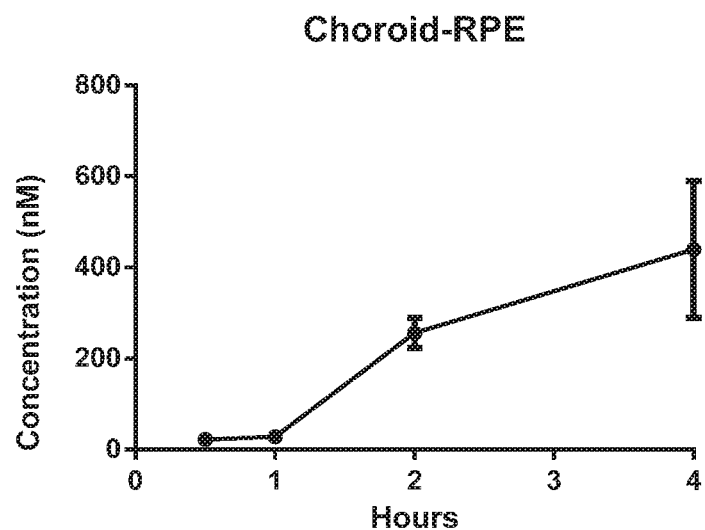
FIG. 9 is a PK profile for Crystalline Form II of Compound 5 in choroid-RPE (retinal pigment epithiluem) tissue of Gottingen mini-pig after topical administration.
Figure 10:
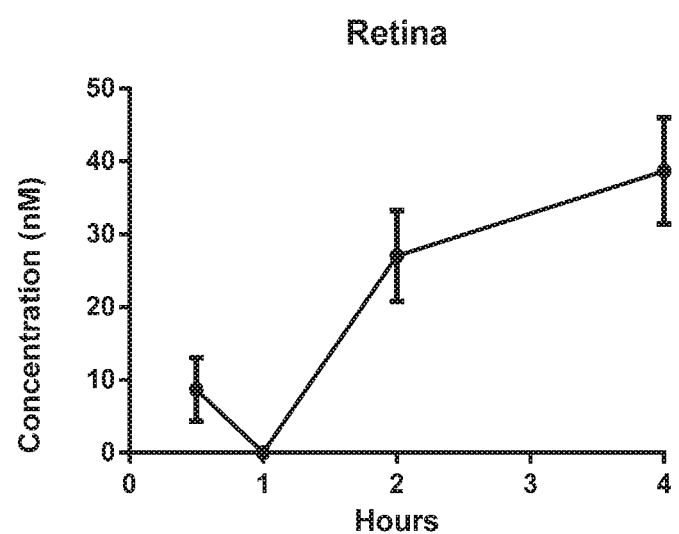
FIG. 10 is a PK profile for Crystalline Form II of Compound 5 in retina tissue of Gottingen mini-pig after topical administration.
Figure 11:
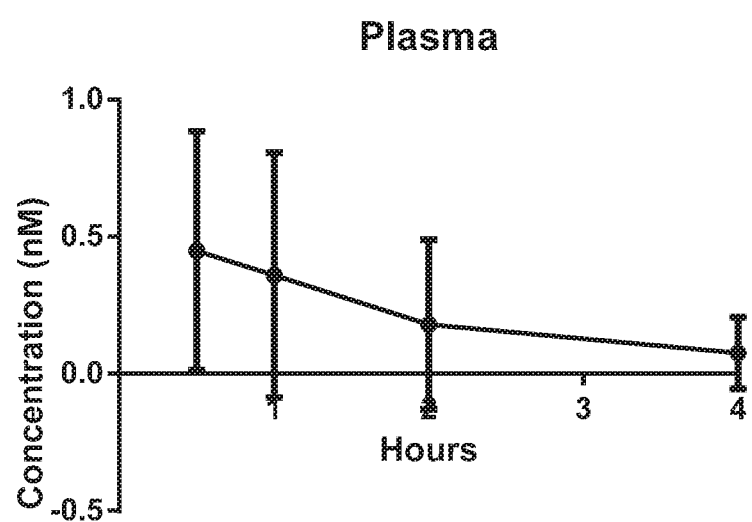
FIG. 11 is a PK profile for Crystalline Form II of Compound 5 in plasma of Gottingen mini-pig after topical administration.

The resulting drug exposures in plasma and in the back of the eye are shown in FIGS. 9, 10 and 11. These results demonstrate that topical instillation of crystalline Form II of Compound 5 as MPP results in drug exposure in the retina and choroid in vivo.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A crystalline form of Compound 5:

(Compound 5)

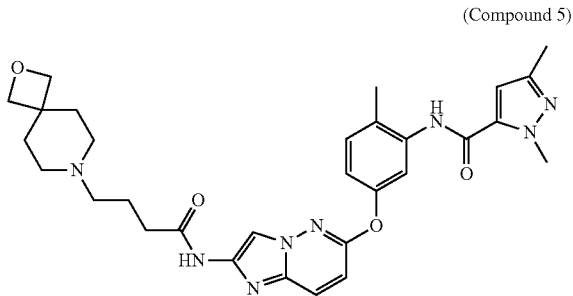 [SMILES: Cc1cc(C(=O)Nc2cc(Oc3ccc4nc(NC(=O)CCCN5CCC6(CC5)COC6)cn4n3)ccc2C)n(C)n1]

wherein the crystalline form is crystalline Form I, wherein the crystalline Form I has an X-ray powder diffraction (XRPD) pattern with a largest peak at about 4.31±0.2 degrees 2θ and a second largest peak at about 6.30±0.2 degrees 2θ, wherein the X-ray source is a Cu/Kα source.

2. A crystalline form of Compound 5, (Compound 5)

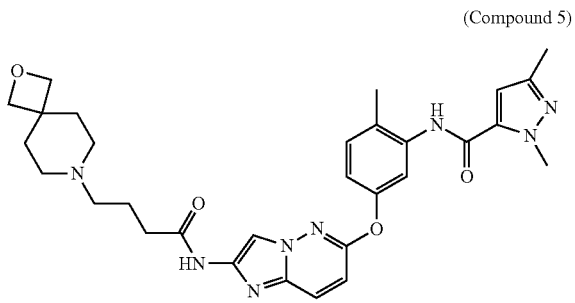 [SMILES: Cc1cc(C(=O)Nc2cc(Oc3ccc4nc(NC(=O)CCCN5CCC6(CC5)COC6)cn4n3)ccc2C)n(C)n1]

wherein the crystalline form is crystalline Form II, wherein the crystalline Form II has an X-ray powder diffraction (XRPD) pattern with a largest peak at about 4.59±0.2 degrees 2θ and a second largest peak at about 3.42±0.2 degrees 2θ, wherein the X-ray source is a Cu/Kα source.

3. A process for preparing a crystalline form of claim 2, comprising:
mixing crystalline Form I of Compound 5 with a solution of acetonitrile and water;
heating the solution to dissolve Compound 5 and then allowing the solution to cool; and
recovering crystalline Form II of Compound 5 from the solution.

4. The process of claim 3, wherein the solution comprises a 90:10 acetonitrile:water mixture.

5. A pharmaceutical composition comprising a crystalline form of claim 1 or 2, and a pharmaceutically acceptable carrier.

6. The pharmaceutical composition of claim 5, wherein the pharmaceutical composition is suitable for topical administration, injection, oral administration, inhalation, or delivery to the eye.

7. The pharmaceutical composition of claim 6, wherein the pharmaceutical composition is a liquid that is packaged for delivery in eye drop form.

8. A method of treating an ocular disease associated with aberrant signalling of a Vascular Endothelial Growth Factor (VEGF) signalling pathway, comprising administering to a subject in need thereof a therapeutically effective amount of the crystalline form of claim 1 or 2 or the pharmaceutical composition of claim 5, wherein the ocular disease is retinopathy, age-related macular degeneration, corneal neovascularization, diabetic macular edema, cystoid macular edema, or retinal vein occlusion.

* * * * *